(12) United States Patent
Gunderson

(10) Patent No.: US 9,561,377 B2
(45) Date of Patent: Feb. 7, 2017

(54) METHOD AND APPARATUS FOR IDENTIFYING LEAD-RELATED CONDITIONS USING PREDICTION AND DETECTION CRITERIA

(75) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1296 days.

(21) Appl. No.: 12/057,562

(22) Filed: Mar. 28, 2008

(65) Prior Publication Data

US 2008/0215110 A1 Sep. 4, 2008

Related U.S. Application Data

(63) Continuation of application No. 11/115,607, filed on Apr. 27, 2005, now Pat. No. 7,369,893.

(60) Provisional application No. 60/632,000, filed on Dec. 1, 2004.

(51) Int. Cl.
*A61N 1/08* (2006.01)
*A61N 1/37* (2006.01)
*A61N 1/39* (2006.01)
*A61N 1/362* (2006.01)

(52) U.S. Cl.
CPC ........... *A61N 1/3704* (2013.01); *A61N 1/3706* (2013.01); *A61N 1/3925* (2013.01); *A61N 1/3621* (2013.01); *A61N 2001/083* (2013.01)

(58) Field of Classification Search
USPC ........................................ 607/2, 27, 28, 116
See application file for complete search history.

(56) References Cited

U.S. PATENT DOCUMENTS

| | | | |
|---|---|---|---|
| 4,374,382 A | | 2/1983 | Markowitz |
| 4,428,378 A | | 1/1984 | Anderson et al. |
| 5,107,833 A | | 4/1992 | Barsness |
| 5,117,824 A | | 6/1992 | Keimel et al. |
| 5,168,871 A | | 12/1992 | Grevious |
| 5,292,343 A | | 3/1994 | Blanchette et al. |
| 5,314,450 A | | 5/1994 | Thompson |
| 5,324,315 A | | 6/1994 | Grevious |
| 5,339,820 A | | 8/1994 | Henry et al. |
| 5,354,319 A | | 10/1994 | Wyborny et al. |
| 5,383,909 A | | 1/1995 | Keimel |
| 5,403,352 A | | 4/1995 | Rossing |
| 5,513,644 A | | 5/1996 | McClure et al. |
| 5,545,186 A | | 8/1996 | Olson et al. |
| 5,755,736 A | | 5/1998 | Gillberg et al. |
| 5,776,168 A | | 7/1998 | Gunderson |
| 5,814,088 A | * | 9/1998 | Paul et al. ..................... 607/28 |
| 5,910,156 A | | 6/1999 | Cinbis et al. |
| 6,317,633 B1 | * | 11/2001 | Jorgenson et al. ............ 607/28 |
| 6,721,600 B2 | * | 4/2004 | Jorgenson et al. ............ 607/27 |
| 7,266,409 B2 | | 9/2007 | Gunderson |
| 2001/0031997 A1 | | 10/2001 | Lee |
| 2001/0037366 A1 | | 11/2001 | Webb et al. |
| 2002/0120307 A1 | | 8/2002 | Jorgenson et al. |
| 2003/0204215 A1 | * | 10/2003 | Gunderson et al. ........... 607/27 |

(Continued)

*Primary Examiner* — Erica Lee

(57) ABSTRACT

A method for delivering therapy in a medical device includes a two-tiered approach of determining the presence of a lead-related condition, and determining, in response to a lead-related condition being present, the presence of oversensing. Delivery of therapy by the medical device is controlled in response to determining that both the lead-related condition and oversensing are present.

23 Claims, 21 Drawing Sheets

(56) References Cited

U.S. PATENT DOCUMENTS

| | | |
|---|---|---|
| 2004/0015197 A1 | 1/2004 | Gunderson |
| 2004/0064161 A1* | 4/2004 | Gunderson et al. |
| 2004/0230233 A1* | 11/2004 | Gunderson et al. ............ 607/9 |
| 2005/0137636 A1* | 6/2005 | Gunderson .......... A61N 1/3706 607/27 |
| 2006/0116732 A1 | 6/2006 | Gunderson et al. |
| 2008/0172098 A1 | 7/2008 | Gunderson |

* cited by examiner

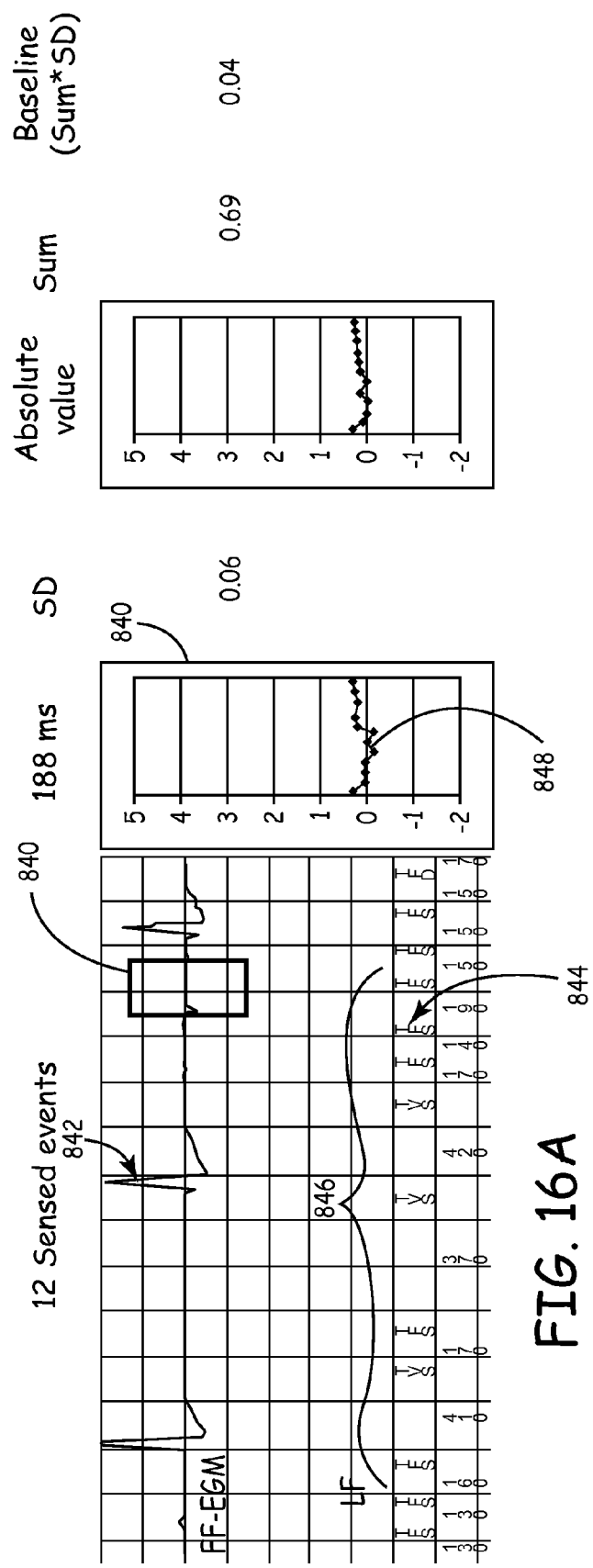

METHOD AND APPARATUS FOR IDENTIFYING LEAD-RELATED CONDITIONS USING PREDICTION AND DETECTION CRITERIA

RELATED APPLICATION

This application is a continuation of application Ser. No. 11/115,607, filed Apr. 27, 2005now U.S. Pat. No. 7,369,893; now allowed, which claims priority and other benefits from U.S. Provisional Patent Application Ser. No. 60/632,000, filed Dec. 1, 2004, entitled "IDENTIFICATION OF OVERSENSING IN A MEDICAL DEVICE", incorporated herein by reference in its entirety. Cross-reference is hereby made to commonly assigned related U.S. patent application Ser. No. 10/436,626, filed May 13, 2003, and U.S. patent application Ser. No. 10/818,098, filed Dec. 4, 2003, incorporated herein by reference in their entireties.

FIELD OF THE INVENTION

The present invention relates generally to implantable medical devices, and in particular to a method for automatically identifying lead-related conditions based on lead impedance measurement trends and oversensing parameters.

BACKGROUND OF THE INVENTION

A wide variety of implantable medical devices for delivering a therapy or monitoring a physiologic condition which may employ one or more elongated electrical leads and/or sensors have been clinically implanted or proposed for clinical implantation in patients. Such implantable medical devices may deliver therapy or monitor the heart, muscle, nerve, brain, stomach or other organs. Implantable medical devices such as pacemakers and implantable cardioverter defibrillators (ICDs), are available for arresting cardiac arrhythmias by delivering electrical impulses to the heart. Such devices sense the heart's intrinsic rhythm through cardiac leads carrying electrodes that may be implanted in the heart. When an abnormal rhythm is detected, which may be bradycardia, tachycardia or fibrillation, an appropriate electrical therapy is delivered to restore the heart's normal rhythm.

Leads associated with such implantable medical devices typically include a lead body extending between a proximal lead end and a distal lead end and incorporates one or more exposed electrode or sensor elements located at or near the distal lead end. One or more elongated electrical conductors extend through the lead body from a connector assembly provided at a proximal lead end for connection with an associated implantable medical device and an electrode located at the distal lead end or along a section of the lead body. Each electrical conductor is typically electrically isolated from any other electrical conductors and is encased within an outer sheath that electrically insulates the lead conductors from body tissue and fluids.

Implantable medical device leads may extend from a subcutaneous implantation site of the implantable medical device through an internal body pathway to a desired tissue site. The leads are generally preferred having small diameter, highly flexible, reliable lead bodies that withstand degradation by body fluids and body movements that apply stress and strain to the lead body and the connections made to electrodes. As lead bodies are made smaller and smaller and the number of lead conductors is increased or maintained, problems with lead insulation and integrity of lead conductors may become more prevalent.

Cardiac lead bodies are continuously flexed by the beating of the heart. Other stresses are applied to the lead body during an implantation or lead repositioning procedure. Movements by the patient can cause the route traversed by the lead body to be constricted or otherwise altered causing stresses on the lead body. At times, the lead can be slightly damaged during surgical implantation, and the slight damage may progress in the body environment until a lead conductor fractures and/or the insulation is breached. The effects of lead body damage may progress from an intermittent manifestation to a more continuous lead related condition. In extreme cases, insulation of one or more of the electrical conductors may be breached, causing the conductors to contact one another or with body fluids resulting in a low impedance or short circuit. In other cases, a lead conductor may fracture and exhibit an intermittent or continuous open circuit resulting in an intermittent or continuous high impedance.

Other problems can arise at the proximal lead end where the electrical connection between implantable medical device connector elements and the lead connector elements may be intermittently or continuously disrupted, resulting in a high impedance or open circuit. Usually, such connector open circuit problems result from insufficient tightening of connection mechanisms, such as a set screw, at the time of implantation followed by a gradual loosening of the connection until contact becomes intermittent or open or an incomplete lead pin insertion.

Such lead problems resulting in short or open circuits may be referred to, for simplicity, as "lead related conditions." Typically, it is necessary for an attending clinician to diagnose the nature of a lead-related condition from available data, test routines, and patient symptoms. Then, it is necessary for the clinician to take corrective action, e.g., to either replace the lead, select different electrodes for sensing or pacing, or tighten the proximal connection. In severe cases, the lead-related condition may result in premature depletion of the battery energy of the implantable medical device, requiring its replacement.

In the case of cardiac leads, the ability to sense an intrinsic heart rhythm accurately through a lead can be impaired by any of the above described lead related conditions. Complete lead breakage impedes any sensing functions, lead conductor fractures or intermittent contact can cause electrical noise that interferes with accurate sensing. Oversensing or undersensing can occur resulting in an incorrect interpretation of the heart rhythm by a pacemaker or ICD, potentially resulting in inappropriate withholding or delivery of electrical therapy. For example, oversensing may lead to the detection of tachycardia or fibrillation resulting in the inappropriate delivery of a high voltage shock therapy. Such therapy is painful to the patient and may be experienced repeatedly if a lead related condition is not diagnosed and corrected. Such inappropriate therapies deplete the ICD battery energy prematurely and could inappropriately induce ventricular fibrillation if delivered onto the T-wave.

During cardiac pacing or defibrillation, increased impedance of the stimulation path or the short circuit of lead conductors due to one of the above-described lead related conditions can reduce the effectiveness of a pacing or shocking below that sufficient to pace or defibrillate the heart.

BRIEF DESCRIPTION OF THE DRAWINGS

Various aspects and features of the present invention will be readily appreciated as the same becomes better understood by reference to the following detailed description when considered in connection with the accompanying drawings, in which like reference numerals designate like parts throughout the figures thereof and wherein:

FIGS. 16A and 16B are graphical representations of a determination of a baseline measure of a far-field signal according to an embodiment of the present invention;

DETAILED DESCRIPTION OF THE INVENTION

Figure 1:
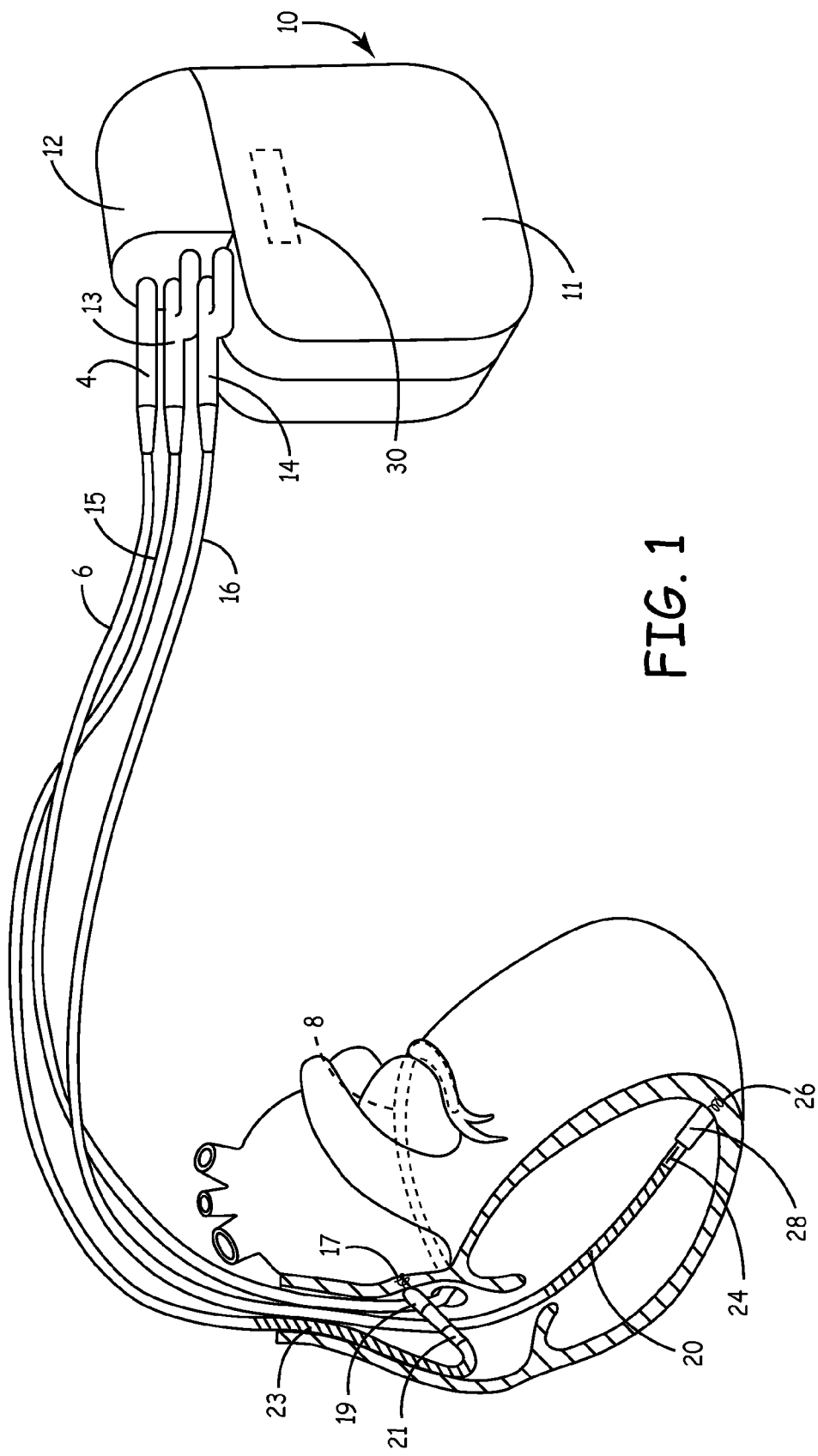
FIG. 1 is a schematic diagram of an exemplary implantable medical device in which the present invention may be usefully practiced.

FIG. 1 is a schematic diagram of a pacemaker/cardioverter/defibrillator and lead set of a type in which the present invention may usefully be practiced. The ventricular lead includes an elongated insulative lead body 16, carrying three mutually insulated conductors. Located adjacent the distal end of the lead are a ring electrode 24, an extendable helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. At the proximal end of the lead is a bifurcated connector 14, which carries three electrical connectors, each coupled to one of the coiled conductors.

The atrial/SVC lead includes an elongated insulative lead body 15, also carrying three mutually insulated conductors. Located adjacent the J-shaped distal end of the lead are a ring electrode 21 and an extendible helix electrode 17, mounted retractably within an insulative electrode head 19. Each of the electrodes is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. At the proximal end of the lead is a bifurcated connector 13, which carries three electrical connectors, each coupled to one of the coiled conductors.

The coronary sinus lead includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector plug 4 that carries an electrical connector, coupled to the coiled conductor.

The pacemaker/cardioverter/defibrillator 10 includes a hermetic enclosure or housing 11 containing the electronic circuitry used for generating cardiac pacing pulses for delivering cardioversion and defibrillation shocks and for monitoring the patient's heart rhythm. Pacemaker/cardioverter/defibrillator 10 is shown with the lead connector assemblies 4, 13 and 14 inserted into the connector block 12, which serves as a receptacle and electrical connector for receiving the connectors 4, 13 and 14 and interconnecting the leads to the circuitry within housing 11. An optional sensor 30 is illustrated schematically by broken outline, and may include one or more of an activity sensor, respiration sensor (potentially from impedance), accelerometer-based posture detector, heart rate detector, ischemia detector and other available physiological sensor known in the art for measuring heart hemodynamics and may be a piezoelectric transducer as known in the art. Sensor 30 may be used, for example, to regulate the underlying pacing rate of the device in rate responsive pacing modes.

Optionally, insulation of the outward facing portion of the housing 11 of the pacemaker/cardioverter/defibrillator 10 may be provided or the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two lead system.

Figure 2:
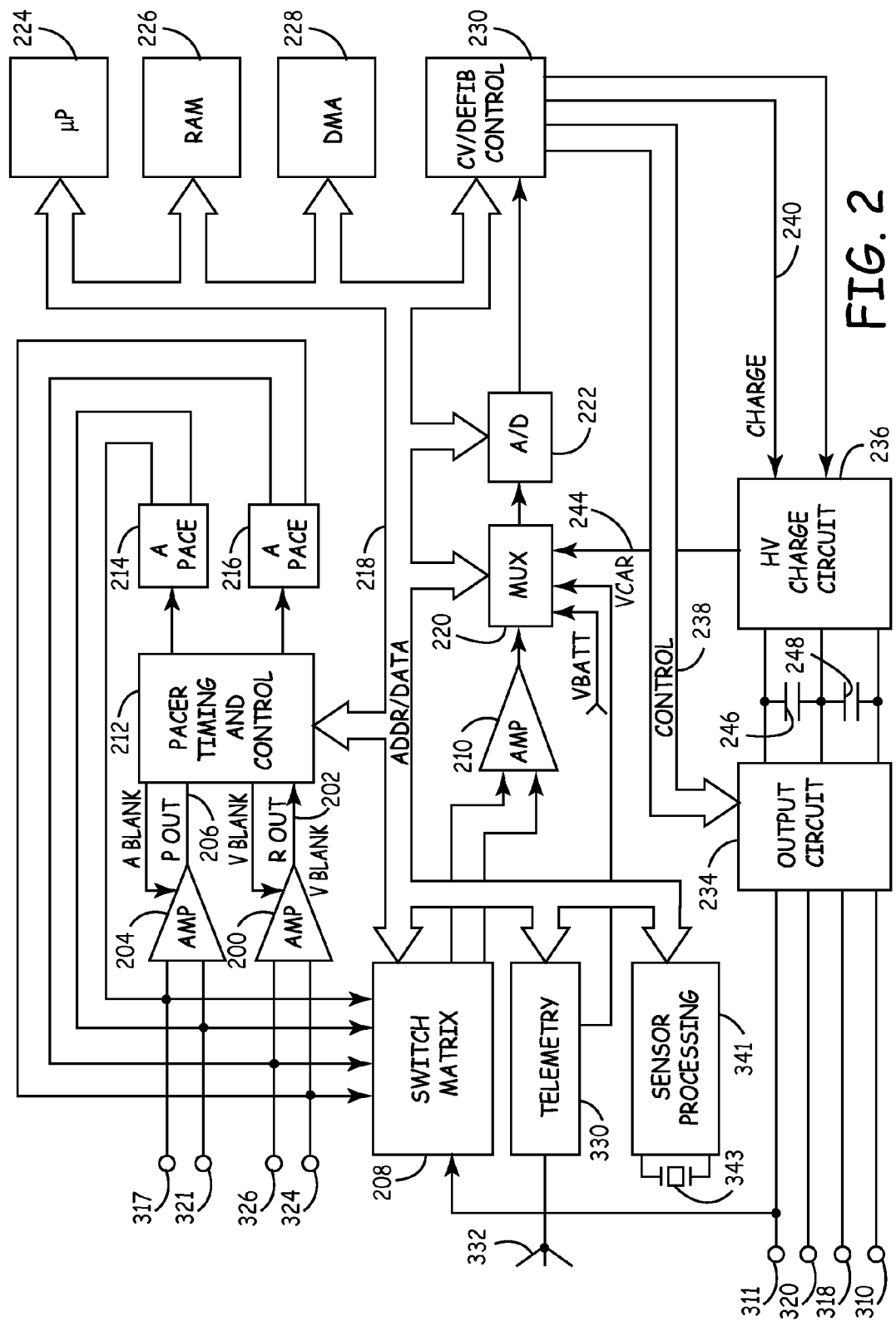
FIG. 2 is a functional, block diagram of the implantable medical device of FIG. 1, in which methods included in the present invention may be implemented.

FIG. 2 is a functional schematic diagram of an implantable pacemaker/cardioverter/defibrillator of the type illustrated in FIG. 1, in which the present invention may usefully be practiced. This diagram should be taken as exemplary of one type of anti-tachyarrhythmia device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to an electrode formed along the uninsulated portion of the housing of the implantable pacemaker/cardioverter/defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A v-sense signal is generated on R-out line 202 whenever the signal sensed between electrodes 324 and 326 exceeds the present sensing threshold.

Electrodes 317 and 321 are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety. However, any of the numerous prior art sense amplifiers employed in implantable cardiac pacemakers, defibrillators and monitors may also usefully be employed in conjunction with the present invention.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits 200, 204 produce atrial and ventricular EGM signals which also may be digitized and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, incorporated by reference herein in its entirety. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

The device of FIG. 2 includes an optional activity sensor 343, mounted to the interior surface of the device housing or to the hybrid circuit within the device housing and corresponds to sensor 30 of FIG. 1. The sensor 343 and sensor present in circuitry 341 may be employed in the conventional fashion described in U.S. Pat. No. 4,428,378 issued to Anderson et al, incorporated herein by reference in its entirety, to regulate the underlying pacing rate of the device in rate responsive pacing modes.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, MI, DDI, DDDR, VVIR, DVIR, VDDR, AAIR, DDIR and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and are used in conjunction with the present invention to determine oversensing and in conjunction with tachyarrhythmia detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present invention may include any of the numerous available prior art tachyarrhythmia detection algorithms. One preferred embodiment may employ all or a subset of the rule-based detection methods described in U.S. Pat. No. 5,545,186 issued to Olson et al. or in U.S. Pat. No. 5,755,736 issued to Gillberg et al., both incorporated herein by reference in their entireties. However, any of the various arrhythmia detection methodologies known to the art might also usefully be employed in alternative embodiments of the invention.

In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

Figure 3:
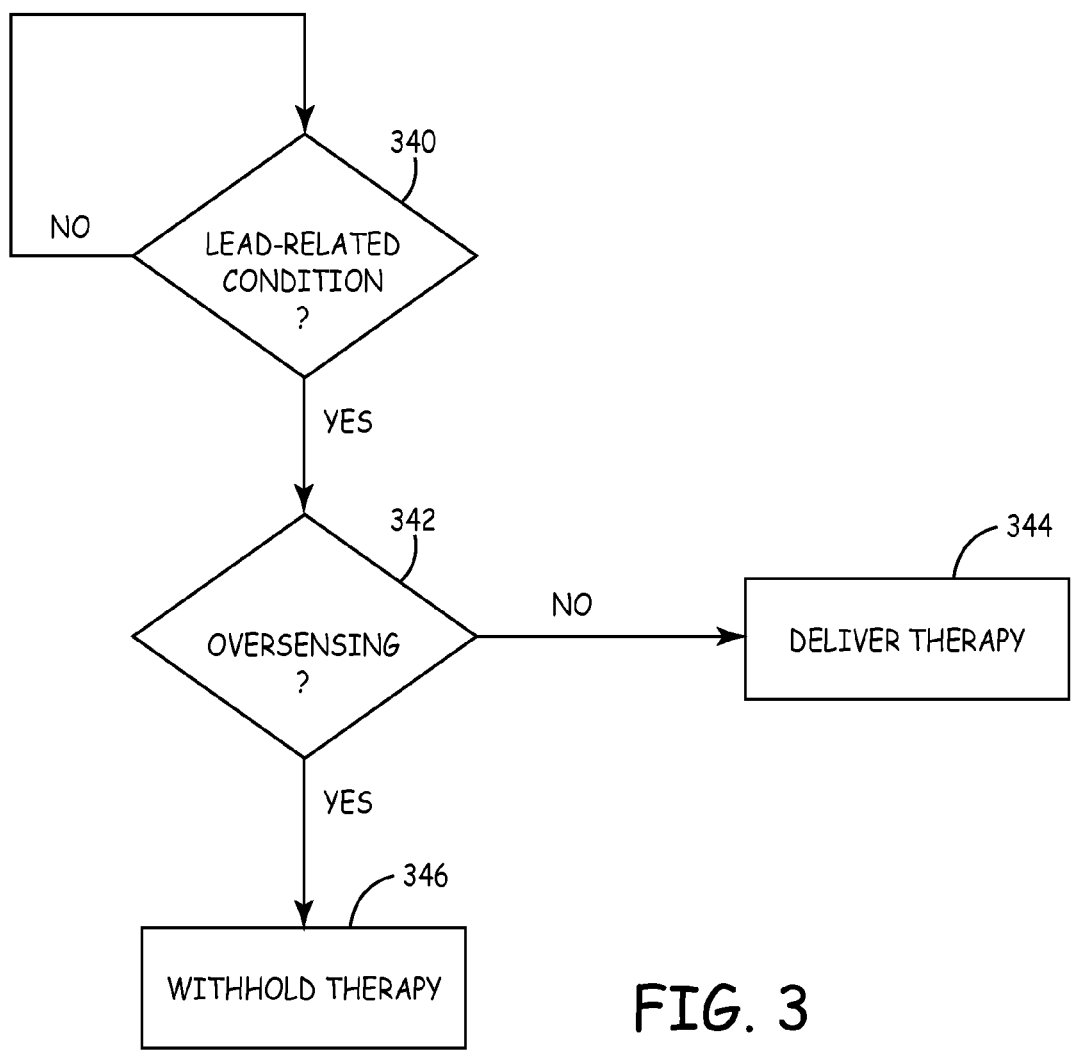
FIG. 3 is a flow chart of a method for delivering therapy in a medical device, according to the present invention.

FIG. 3 is a flow chart of a method for delivering therapy in a medical device, according to the present invention. As illustrated in FIG. 3, in order to reduce the delivery of inappropriate therapy due to lead-related problems, a method for delivering therapy in a medical device according to an embodiment of the present invention includes first predicting the presence of a lead-related condition, Block 340, and once the presence of a lead-related condition is detected, determining whether oversensing is likely taking place, Block 342. If oversensing is likely occurring, the delivery of therapy, such as shock therapy, for example, is withheld, Block 346. On the other hand, if oversensing is not likely occurring, normal delivery of the therapy takes place, Block 344. Thus, the present invention provides a two-tiered approach for reducing delivery of shock due to lead-related conditions by combining an early warning prediction algorithm (e.g., two weeks prior to VF detection) and identification of inappropriate VF detection due to oversensing caused by a lead related condition. After satisfying the prediction algorithm, Block 340, selected parameters (e.g., EGM storage) could be changed that are to be used by the inappropriate detection algorithm (e.g., RV coil to can EGM), Block 342. Therapy is subsequently withheld only if both the prediction of the presence of a lead related condition is satisfied and the determination that oversensing is likely taking place is satisfied.

Figure 4:
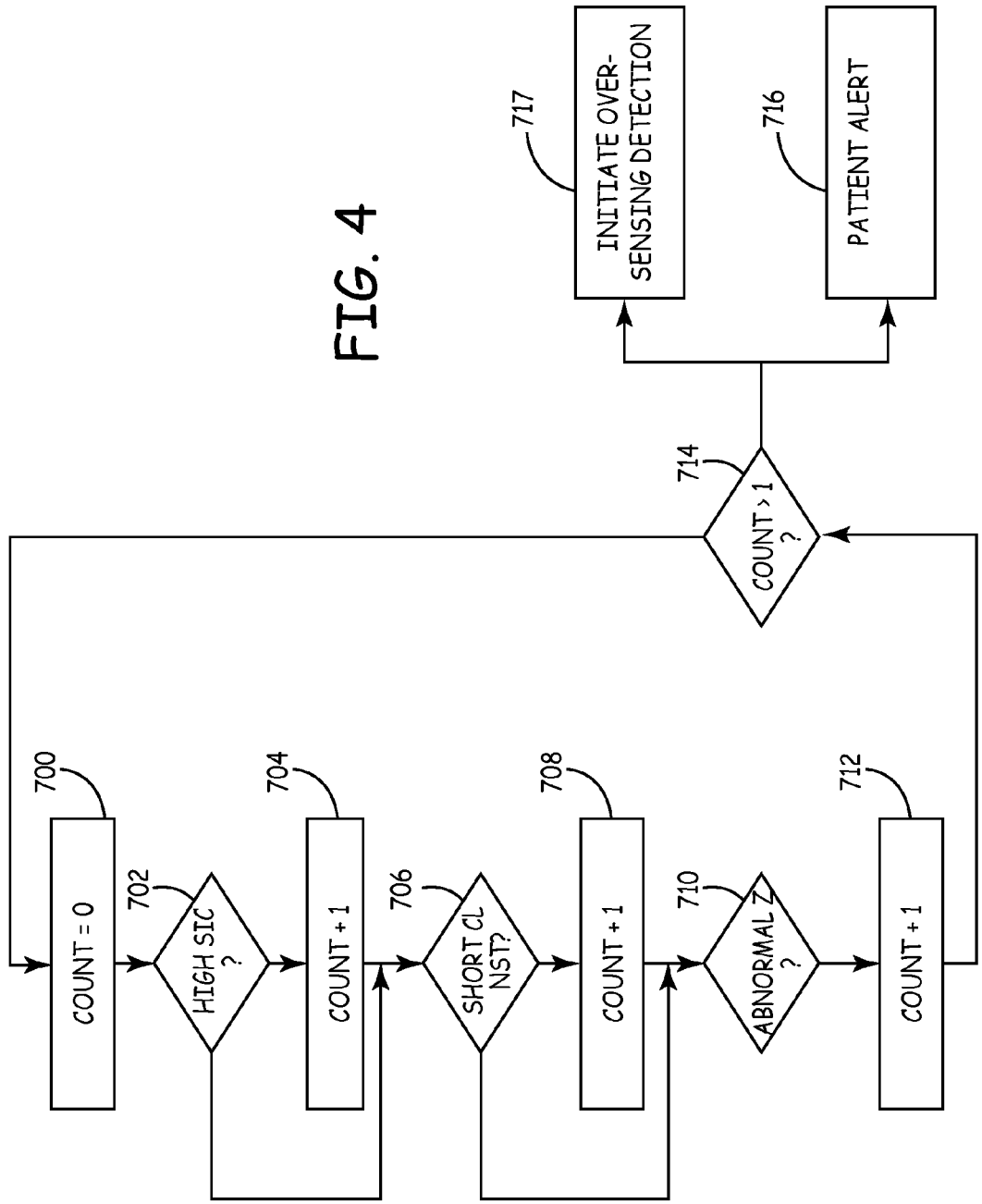
FIG. 4 is a flow chart of a method for detecting a lead-related condiction in a method for delivering therapy according to an embodiment of the present invention.

FIG. 4 is a flow chart of a method for detecting a lead-related condiction in a method for delivering therapy according to an embodiment of the present invention. As illustrated in FIG. 4, once a method for detecting a lead-related condition (Block 340 of FIG. 3) is initiated, a criteria counter is set equal to zero, Block 700, and a determination is made as to whether a first oversensing criteria is satisfied, such as whether a sensing integrity counter has been satisfied, Block 702. If the first oversensing criteria is satisfied, as will be described below in detail, the criteria counter is incremented, Block 704. Once either the first oversensing criteria is determined to have been satisfied and the criteria counter has been incremented, or the first oversensing criteria is determined not to be satisfied, a determination is made as to whether a second oversensing criteria, such as a non-sustained event counter, is satisfied, Block 706. If the second oversensing criteria is satisfied, as will be described in detail below, the criteria counter is incremented, Block 708. Once either the second oversensing criteria is determined to have been satisfied and the criteria counter has been incremented, or the second oversensing criteria is determined not to be satisfied, a determination is made as to whether an impedance criteria determined using the methods described above is satisfied, Block 710. If the impedance criteria is satisfied, the criteria counter is incremented, Block 712. Once either the impedance criteria is determined to have been satisfied and the criteria counter has been incremented, or the impedance criteria is determined not to be satisfied, a determination is made as to whether more than one of the criteria has been met, Block 714.

If it is determined that more than one of the criteria have been met, such as both of the oversensing criteria or at least one of the oversensing criteria and impedance criteria, the likelihood of a lead related condition is saisfied, and a determination as to whether oversensing is likely occurring is initiated, Block 717, which is described below in reference to FIGS. 13-18. In addition to initiating the determination of the likelihood of oversensing occurring, Block 717, a patient alert is also triggered, Block 716, once the determination that more than one of the criteria have been met, YES in Block 714. According to the present invention, the patient alert may be implemented in an implantable medical device implanted within the patient or may be implemented on a network server, as will be described below.

Figure 5:
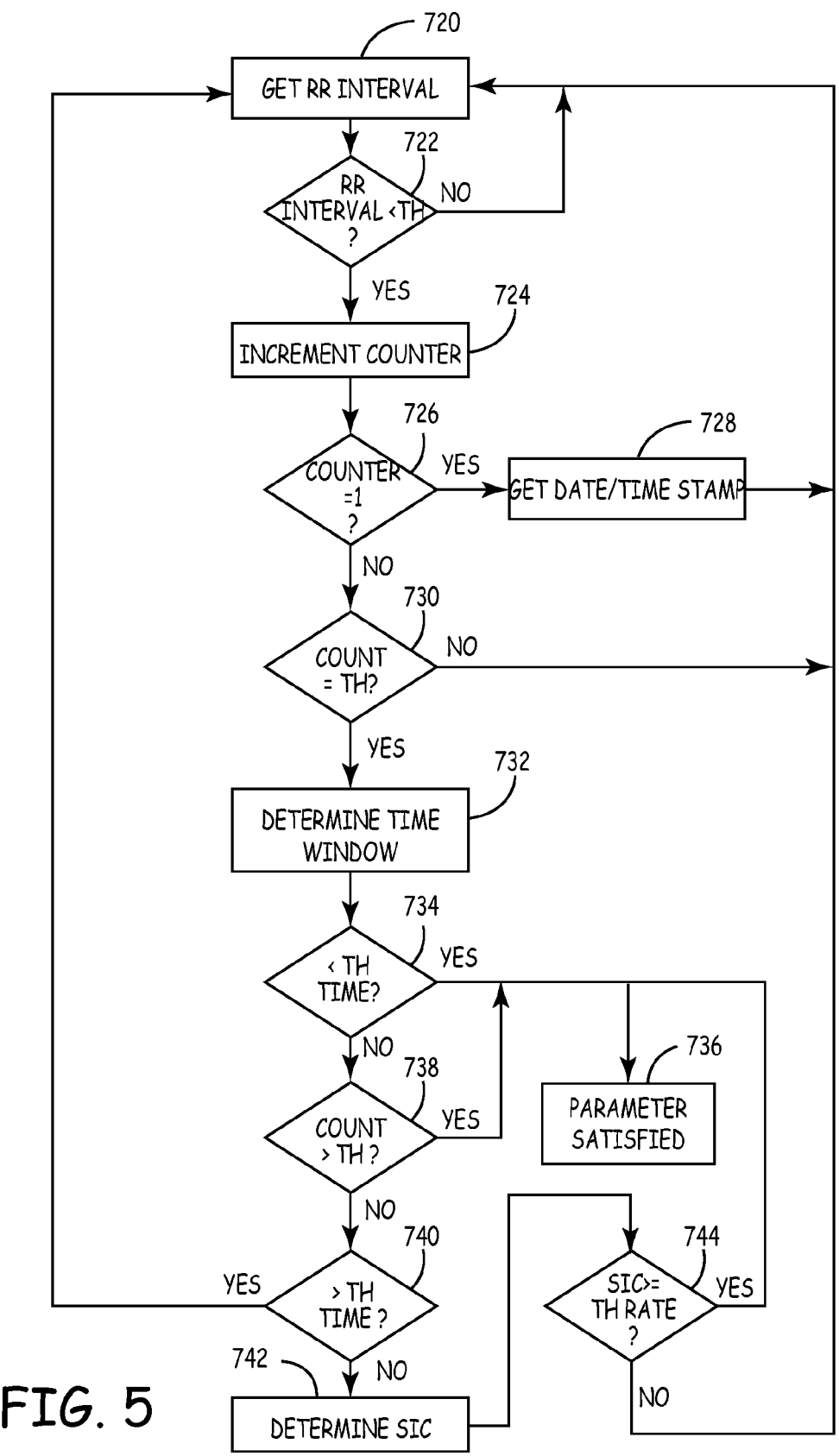
FIG. 5 is a flowchart of a method for determining whether an oversensing criteria has been satisfied during detection of a lead-related condition according to an embodiment of the present invention.

FIG. 5 is a flowchart of a method for determining whether an oversensing criteria has been satisfied during detection of a lead-related condition according to an embodiment of the present invention. As illustrated in FIG. 5, according to an embodiment of the present invention, in order to determine whether the sensing integrity counter has been satisfied in Block 702 in the method for detecting a lead-related condition of FIG. 4, a next RR-interval is determined, Block 720, and a determination is made as to whether the RR-interval is less than a predetermined threshold, Block 722. Since oversensing due to a lead related problem often occurs near the blanking period of the sense amplifier, the sensing integrity counter quantifies this oversensing by counting the number of RR-intervals that are determined to be less than a predetermined time period above the blanking period, such as 20 ms above the blanking period, for example. Since, in certain devices, the blanking period is set as 120 ms, the predetermined threshold of Block 722 would therefore be equal to approximately 140 ms, for example. According to an embodiment of the present invention, in devices in which the blanking period is programmable and can therefore have a value other than 120 ms, the predetermined threshold in Block 722 is simply set equal to the programmed blanking period plus 20 ms, with a maximum value of 170 ms, for example. While the predetermined time that the threshold is set above the blanking period is described as being 20 ms, it is understood that the present invention is not intended to be limited 20 ms, but rather, would include using any other desired time period.

If the RR-interval is not less than the predetermined threshold, and therefore is not near the blanking period, i.e., within 20 ms of the blanking period, a next RR-interval is obtained, Block 720, and a determination is made as to whether the next RR-interval is less than the predetermined threshold, Block 722. Each time that the current RR-interval is determined to be less than the predetermined threshold and therefore near the blanking period, a counter is incremented, Block 724. If the current RR-interval is the initial RR-interval determined to be near the blanking period for the current session, i.e., the counter is equal to one in Block 726, a date/time stamp since the last session is obtained from the timing and control circuitry 212, for example, to determine a start time of the current session, Block 728.

Once the session start time is determined, a next RR-interval is obtained, Block 720, and the process is repeated, with a determination being made as to whether the next RR-interval is less than the predetermined threshold, Block 722. If the current RR-interval is not the initial RR-interval determined to be near the blanking period for the current session, i.e., the counter is not equal to one in Block 726, a determination is made as to whether the number of RR-intervals that are near the blanking period, i.e., less than the threshold in Block 722, is equal to a predetermined threshold number, Block 730. If less than the predetermined threshold number of RR-intervals are near the blanking period, NO in Block 730, a next RR-interval is obtained, Block 720, and the process is repeated, with a determination being made as to whether the next RR-interval is less than the predetermined threshold, Block 722.

Once the number of RR-intervals that are near the blanking period is equal to the predetermined threshold number, YES in Block 730, a current time window duration is determined by taking the difference between the start time of the current session obtained in Block 728 and the current date/time stamp obtained from the timing and control circuitry 212, Block 732. Once the current time window duration is determined, a determination is made as whether the current time window duration is less than or equal to a threshold time window, Block 734. If the time duration window is less than or equal to the threshold time window, the oversensing criteria is determined to be satisfied, Block 736, and therefore the criteria counter, Block 704 of FIG. 4, is incremented.

According to an embodiment of the present invention, the predetermined threshold number utilized in Block 730 is set equal to thirty and the threshold time window is set equal to three days for Block 734, so that one way in which the oversensing criteria is satisfied and therefore the oversensing criteria counter is incremented is if thirty RR-intervals are determined to be near the blanking period within the first three days, for example. However, any desired values for the predetermined threshold number of Block 730 and the threshold time window of Block 734 without departing from the present invention. According to the present invention, the predetermined threshold number utilized in Block 730 is given a value corresponding to an indication that a mechanical problem associated with the lead is present, such as a loose set screw, and is therefore set equal to thirty, for example, although any desired value may be utilized. In addition, although three days is utilized in Block 734, any desired number of days or other time period may be utilized.

If the time duration window is greater than the threshold time window, NO in Block 734, a determination is made as to whether the number of RR-intervals determined to be near the blanking period during the current session is greater than a second predetermined threshold number, Block 738, by determining whether the counter in Block 724 is greater than the second predetermined threshold number of Block 738. According to an embodiment of the present invention, the second predetermined threshold number of Block 738 is set as 300, for example, although any threshold value may be chosen. If the number of RR-intervals near the blanking period is greater than the second threshold, the oversensing criteria is determined to be satisfied, Block 736, and the criteria counter, Block 704 of FIG. 4, is incremented. If the number of RR-intervals near the blanking period is less than or equal to the second threshold, No in Block 738, a determination is made as to whether the time duration window is greater than a second threshold time period, such as 30 days, for example, Block 740.

If the time duration window is not greater than the second threshold time period, an average sensing integrity counter per day is determined, Block 742, by dividing the count of the number of RR-intervals determined to be near the blanking period, Block 724, by the current time window duration determined in Block 732. A determination is then made as to whether the average sensing integrity counter per day is greater than or equal to a predetermined threshold rate, such as 10 per day, for example, Block 744, although the predetermined threshold rate in Block 744 could have any desired value associated with an indication of a lead-related condition. If the average sensing integrity counter per day is greater than or equal to the predetermined threshold rate, the oversensing criteria is determined to be satisfied, Block 736, and therefore the criteria counter, Block 704 of FIG. 4, is incremented. If average sensing integrity counter per day is not greater than or equal to the predetermined threshold rate, a next RR-interval is obtained, Block 720, and the process is repeated with a determination being made as to whether the next RR-interval is less than the predetermined threshold, Block 722.

Finally, if the number of RR-intervals near the blanking period is less than or equal to the second threshold, No in Block 738, and the time duration window is greater than the second threshold time period, YES in Block 740, a next RR-interval is obtained, Block 720, and the process is repeated with a determination being made as to whether the next RR-interval is less than the predetermined threshold, Block 722.

Figure 6:
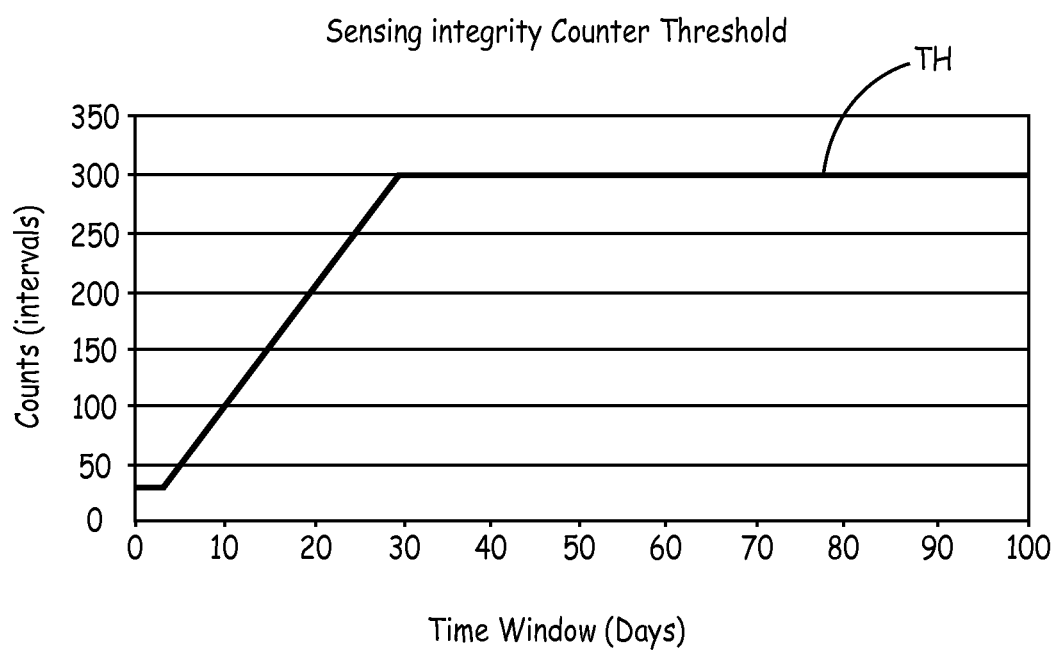
FIG. 6 is a graphical representation of a method for determining whether an oversensing criteria has been satisfied during detection of a lead-related condition according to an embodiment of the present invention.

FIG. 6 is a graphical representation of a method for determining whether an oversensing criteria has been satisfied during detection of a lead-related condition according to an embodiment of the present invention. In this way, as illustrated in FIG. 6, a threshold TH for determining when the sensing integrity criteria is satisfied and therefore the criteria counter of Block 704 of FIG. 4, is incremented, changes at predetermined time periods. In particular, for the first three days of the current session the threshold TH is satisfied once more than thirty RR-intervals are determined to be near the blanking period. Once three days have expired and there have not been thirty RR-intervals determined to be near the blanking period, the threshold is satisfied once there are determined to be an average of ten RR-intervals per day that are determined to be near the blanking period. After thirty days have expired in the current session, the threshold is satisfied once there have been a total of three hundred RR-intervals determined to be near the blanking period.

Figure 7:
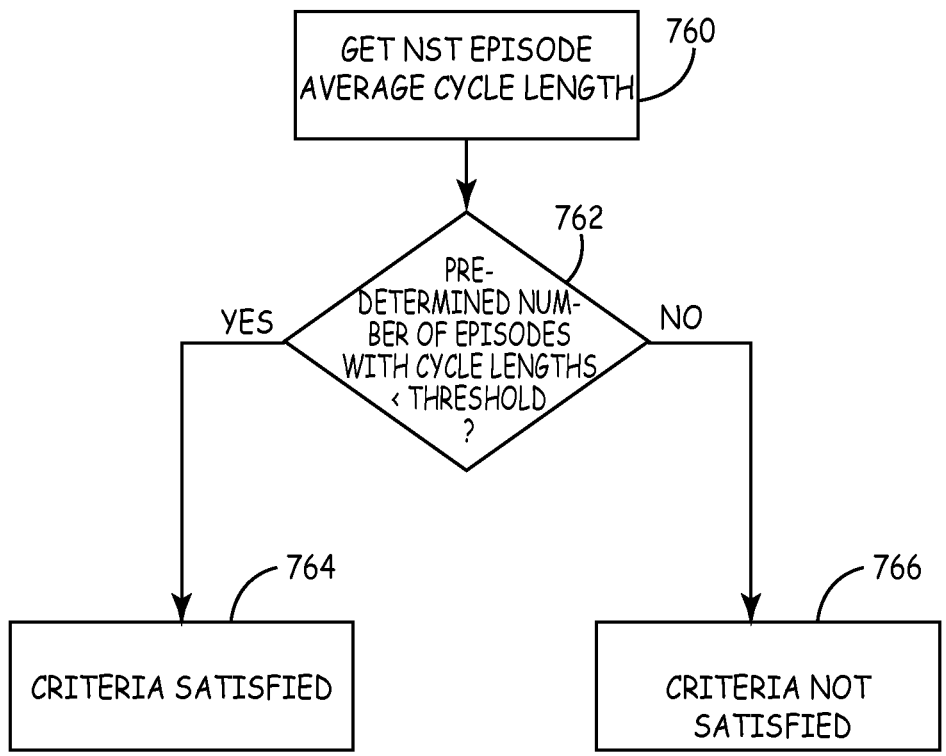
FIG. 7 is a flowchart of a method for determining whether an oversensing criteria has been satisfied during detection of a lead-related condition according to an embodiment of the present invention.

FIG. 7 is a flowchart of a method for determining whether an oversensing criteria has been satisfied during detection of a lead-related condition according to an embodiment of the present invention. As illustrated in FIG. 7, according to an embodiment of the present invention, a second oversensing criteria utilized in the method for detecting a lead related condition relates to identification of non-sustained episodes (Block 706 of FIG. 4). During the normal detection process, the device detects ventricular tachyarrhythmias (VF, VT and FVT) by comparing time intervals between sensed events to a set of programmable detection intervals. For example, when the interval between sensed ventricular events is between 320 and 400 ms, a ventricular tachycardia (VT) interval counter is incremented. Once a certain number events associated with the VT interval are detected, such as 16 events, for example, a VT event is detected and the device responds appropriately.

In addition, a non-sustained ventricular tachycardia event is identified and stored within a non-sustained (NST) episode log when less than the required number of events associated with the VT interval are detected, i.e., less than 16 events, but more than a predetermined number of events associated with the VT interval are identified, such as five for example. The NST epsiode log stores information relating to the non-sustained events, including a date/time stamp and an average cycle length of each non-sustained episode. Because it has been determined that consecutive oversensed events may trigger storage of an inappropriate non-sustained episode in the NST episode log, the present invention utilizes the NST episode log as the second oversensing component in detecting a lead-related condition, as described above in reference to FIG. 4.

For example, as illustrated in FIG. 7, in order to determine whether the second sensing integrity counter has been satisfied in Block 706 of the method for detecting a lead-related condition of FIG. 4, the average cycle lengths for the non-sustained VT events stored in the NST episode log are obtained, Block 760, and a determination is made as to whether there are a predetermined number of non-sustained VT events having average cycle lengths that are less than a predetermined threshold occurring within a predetermined time frame, Block 762. For example, ventricular arrythmia episodes typically have an average cycle length greater than 200 ms and non-sustained episodes with average cycle lengths less than 200 ms are likely due to oversensing. Therefore, according to an embodiment of the present invention, a determination is made in Block 762 as to whether two non-sustained VT events having a cycle length less than 200 ms occur within a one week interval.

If the predetermined number of non-sustained VT events having average cycle lengths that are less than the predetermined threshold occur within the predetermined time frame, the second oversensing criteria is determined to be satisfied, Block 764, and therefore the criteria counter, Block 706 of FIG. 4, is incremented. If there are not the predetermined number of non-sustained VT events having average cycle lengths that are less than the predetermined threshold occurring within the predetermined time frame, the second oversensing criteria is determined not satisfied, Block 766, and the process of detecting a lead-related condition determines whether the other components are satisfied.

Figure 8:
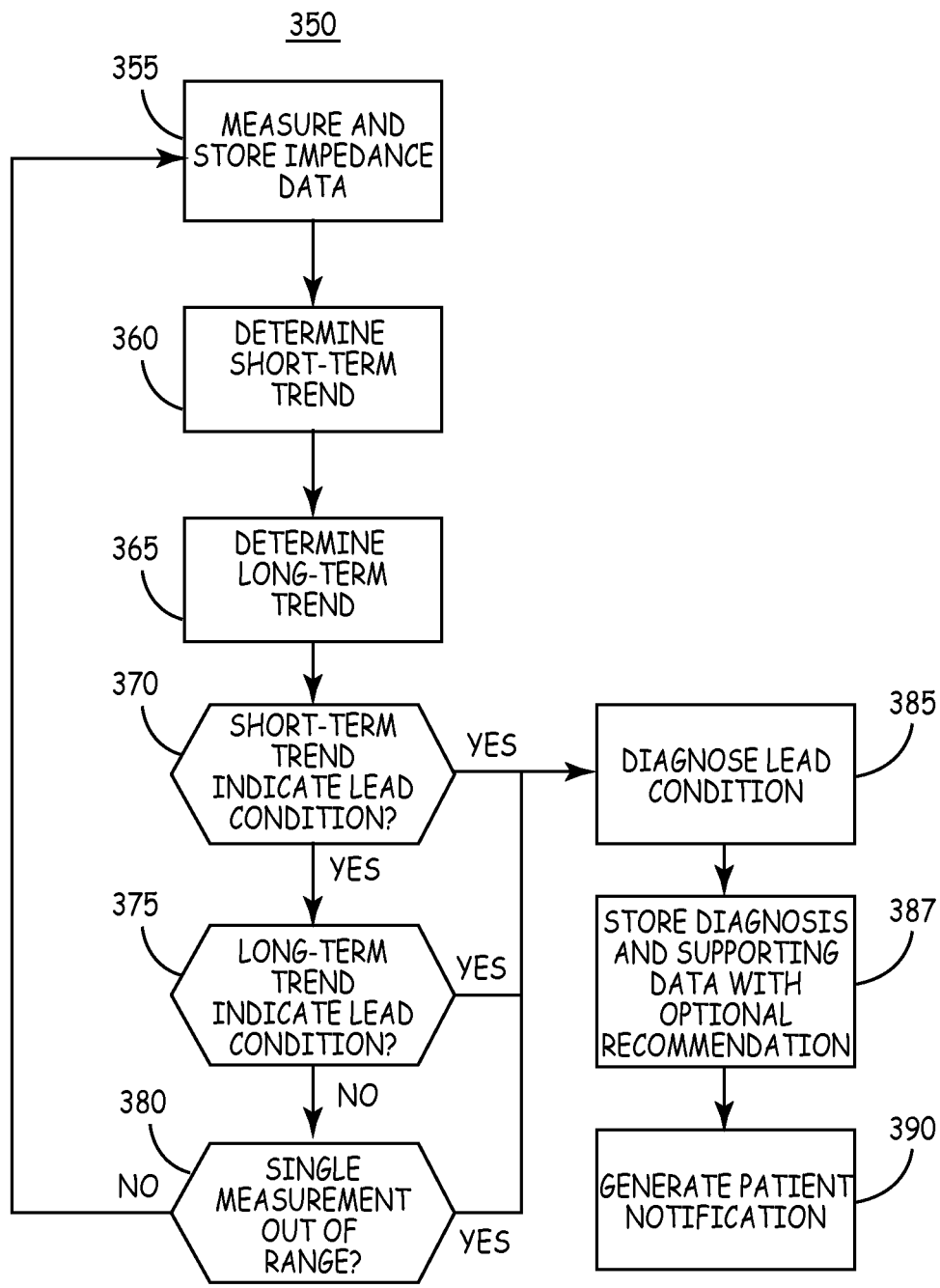
FIG. 8 is a flow chart of monitoring impedance trends for the detection and diagnosis of a lead-related condition according to an embodiment of the present invention.

FIG. 8 is a flow chart of monitoring impedance trends for the detection and diagnosis of a lead-related condition according to an embodiment of the present invention. During the determination of impedance criteria (Block 710 of FIG. 4), for example, lead impedances are measured and stored, Block 355. Lead impedance measurements may be made on a periodic basis, such as at least daily, for example. Multiple periodic impedance measurements may be made depending on the number of leads present and the number of electrodes and conductors carried by each lead. For the configuration shown in FIG. 1, a preferred set of lead impedance measurements includes a low voltage pacing impedance measured across tip electrode 26 and ring electrode 24 and high voltage impedances measured across: 1) ring electrode 24 and can 11, 2) ring electrode 24 and coil electrode 20, 3) tip electrode 26 and coil electrode 20, and 4) tip electrode 26 and can 11.

Based on measured and stored lead impedances, relatively short-term impedance trend parameters are determined at Block 360, and relatively long-term impedance trend parameters are determined at Block 365. These short- and long-term impedance trend parameters are examined at decision Block 370 and 375 to determine if the trends are indicative of a lead-related condition. This examination may include comparing a periodic impedance measurement to impedance trend parameters to determine if diagnostic criteria for detecting a lead-related condition are met. If any of the examined trends are indicative of a lead condition, the condition is diagnosed at Block 385 based on the trend analysis. The diagnosed condition and supporting data may be stored in memory 226 at Block 387 so that a clinician may upload this information to an external device for review. A corrective action may optionally be recommended which may be to check for a loose connection between a lead and the associated IMD or replace a lead or add an additional lead while continuing to use the functioning part of the old lead. At optional Block 390, patient notification signal may be generated so that the patient is aware of a potential problem and seeks medical attention.

As a safety check in case of a sudden lead failure, a most recent lead impedance measurement may be compared to an acceptable range at decision Block 380. An acceptable range may be a predefined range of impedances known to be normal for a particular lead type. If a single measurement is out of the acceptable range, a lead-related condition is diagnosed at Block 385. If no trend or single impedance measurement indicate a lead-related condition as determined at decision Block 370, 375 and 380, the method 350 may operate in a looping fashion by returning to Block 355 to continue measuring and storing impedance data and updating the short-term and long-term impedance trends at Blocks 360 and 365.

Periodic impedance measurements are performed by impedance measurement circuit 204 under the control of microprocessor 224 and are stored in memory 226 of ICD 10. In one embodiment, impedance measurement data may be uplinked to an external device for analysis. Such data storage and transmission is provided in commercially available devices, for example in the GEM® Implantable Cardioverter Defibrillator available from Medtronic, Inc., Minneapolis, Minn. Determination and analysis of impedance trend parameters for detecting a lead-related condition may then be performed by an external device, which may be a programmer or personal computer. Uplinked impedance data may be alternatively be transferred via Internet to a central computer for analysis at a remote location. Reference is made to U.S. Pat. Appln. No. 20010031997 entitled "Instrumentation and software for remote monitoring and programming of implantable medical devices (IMDs)" to Lee, and U.S. Pat. Appln. No. 20010037366 entitled "System and method for providing remote expert communications and video capabilities for use during a medical procedure" to Webb et al., both patent applications being incorporated herein by reference in their entirety. Alternatively, impedance trend parameters may be determined by programs executed by microprocessor 224 and stored in memory 226. Subsequent analysis of impedance trends may be performed by microprocessor 224 or by an external device after uplinking a history of impedance measurements and impedance trend parameters from ICD 10. The operations shown in FIG. 8 may be performed in real-time by ICD 10 such that a lead-related condition may be detected early on and patient notification signal may be generated to alert the patient to seek medical attention. The detected lead-related condition and supporting data may then be uplinked to an external device for review by a physician, who may then take prompt action to confirm and correct the problem.

Figure 9A:
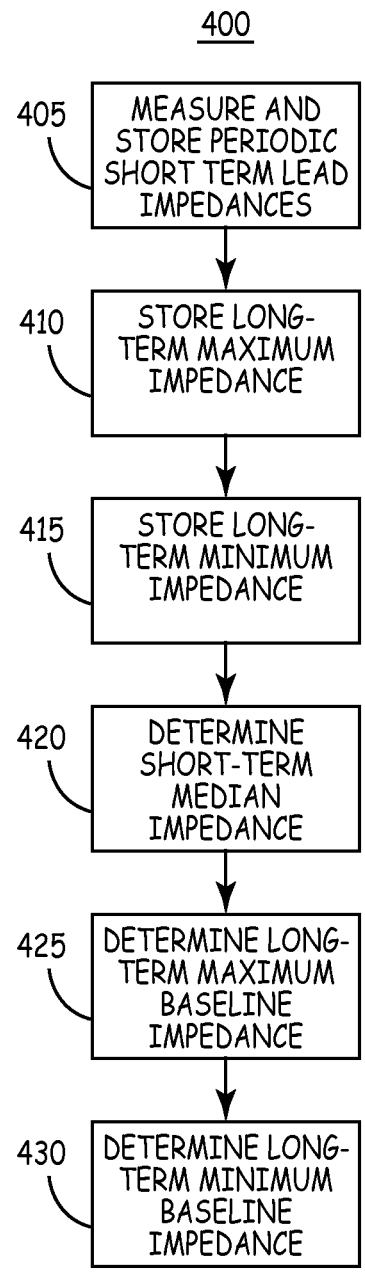
FIG. 9A is a flow chart of a method for determining short-term and long-term impedance trend parameters that may be included in an embodiment of the impedance trend monitoring of FIG. 8.

The operations summarized in FIG. 8 are shown in greater detail in the flow charts of FIGS. 9A through 12. FIG. 9A is a flow chart of a method for determining short-term and long-term impedance trend parameters that may be included in an embodiment of the impedance trend monitoring of FIG. 8. According to an embodiment of the present invention, impedance measurements are made at least daily and each daily impedance measurement is stored in memory 226 at Block 405. A given number of daily (or otherwise periodic) impedance measurements may be stored for a pre-determined term, for example the most recent 14 daily impedance measurements may be stored as short-term impedance measurements for determining a relatively short-term impedance trend.

A relatively longer term is defined for determining long-term impedance trends. According to an embodiment of the present invention, a long-term trend stores weekly measurements over many weeks, such as 1 year for example, or longer. The maximum impedance measurement measured over the relatively longer term and the minimum impedance measurement measured over the relatively longer term are preferably determined as the long-term maximum and long-term minimum impedances. In the method 400 of FIG. 9A, a weekly maximum impedance is determined and stored at Block 410, and a weekly minimum impedance is determined and stored at Block 415.

From the stored daily (short-term) measurements and weekly (long-term) impedance parameters, short-term and long-term trends may be determined. For example, a short-term median impedance is determined at Block 420 from a predetermined number of recent, consecutive periodic measurements. In one embodiment, the median of 14 daily impedance measurements is determined, for example.

Figure 9B:
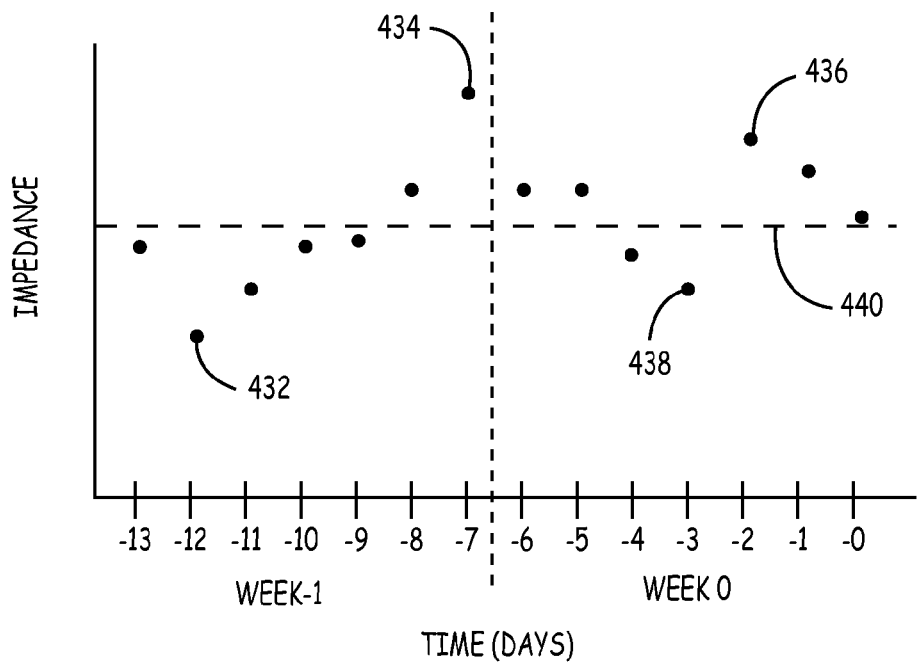
FIG. 9B is a graphical representation of hypothetical daily impedance data generated according to an embodiment of the present invention.

FIG. 9B is a graphical representation of hypothetical daily impedance data generated according to an embodiment of the present invention. As illustrated in FIGS. 9A and 9B, fourteen daily impedance measurements are plotted vs. time, from day 0 through 13 days prior, Block 405. The median daily impedance 440, indicated approximately by dashed line, is then determined in Block 420 from the 14 daily impedance measurements to monitor the trend of the measured short-term impedances. In addition, as described above, a weekly minimum impedance measurement and a weekly maximum impedance measurement is determined using the daily impedance data generated for each week and stored in memory 226. The highest impedance measurement 438 and the lowest impedance measurement 434 made during week 0 are stored as the weekly maximum and minimum impedance measurements, Blocks 410 and 415, respectively, for week 0. Likewise, the highest measurement 434 and lowest measurement 432 made during week −1 are stored as the weekly maximum and minimum impedances, Blocks 410 and 415, respectively, for week −1.

At Block 425 of FIG. 9A, a maximum baseline impedance is determined from stored long-term maximum impedance measurements, Block 410. Similarly, a minimum baseline impedance is determined, Block 430 from stored long-term minimum impedance measurements, Block 415. In one embodiment, trends of long-term maximum impedances and long-term minimum impedances are examined exclusively from each other. However, other algorithms could be designed that combine both maximum and minimum impedances. The maximum and minimum impedance measurements determined over a period of time may deviate significantly from a median measurement if a short or open has occurred along an impedance measurement pathway. For example, if a conductor fracture has occurred, a high impedance may be measured. The high impedance measurement may be intermittent, however, due to motion of the lead body. Periodic impedance measurements for the same pathway, therefore, may continue to fall in a normal range, or close to a median, with occasional high maximum impedance. Intermittent high long-term maximum impedances may therefore occur with a relatively stable minimum long-term impedance.

In another example, if a conductor insulation is breached, a low impedance measurement may occur. Again, a low impedance measurement may be intermittent due to lead movement resulting in some periodic impedance measurements to be relatively normal. Intermittent low long-term minimum impedances may occur with stable long-term maximum impedance. Thus, the trends in the weekly maximum and minimum impedances may be different and mutually exclusive, depending on the type of lead-related condition that may be present. In accordance with the present invention, therefore, a maximum weekly baseline and a minimum weekly baseline are determined to allow mutually exclusive analysis of trends in these parameters.

Figure 9C:
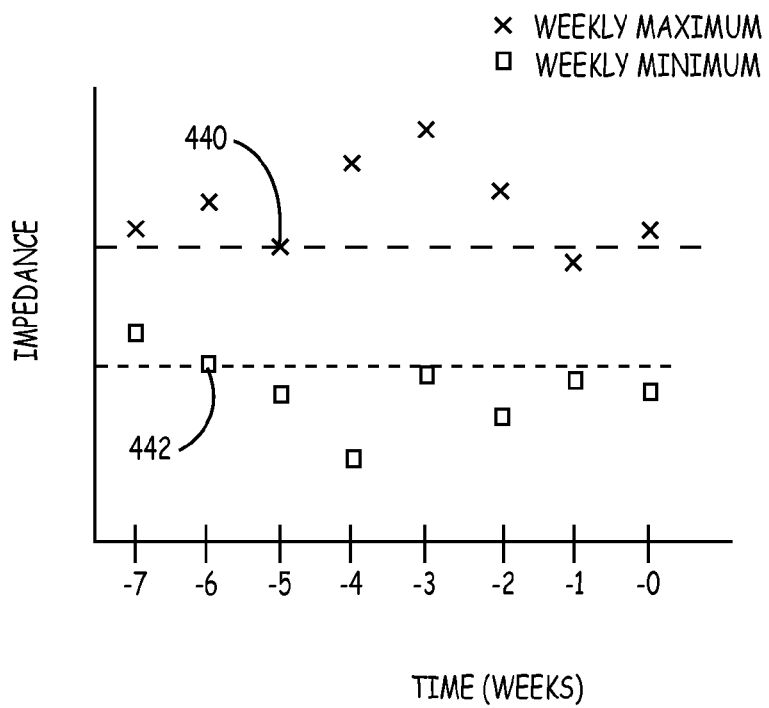
FIG. 9C is a graphical representation of a method for determining long-term maximum and minimum baselines according to an embodiment of the present invention

A long-term maximum baseline impedance, Block 425, and a long-term minimum baseline impedance, Block 430, may be determined based on the long-term maximum and minimum impedance measurements over a given number of terms. FIG. 9C is a graphical representation of a method for determining long-term maximum and minimum baselines according to an embodiment of the present invention. As illustrated in FIG. 9C, 8 weeks of maximum and minimum weekly impedance values, for example, are plotted vs. time, from week 0 through 7 weeks prior, although any number of weeks may be utilized. A long-term maximum baseline impedance 441 is determined as the second lowest weekly maximum impedance determined from the 8 weekly maximum impedance measurements. A long-term minimum baseline 442 is determined as the second highest weekly minimum impedance determined from 8 weekly minimum impedance measurements. By using the second lowest and second highest maximum or minimum impedance measurement for setting a maximum or minimum baseline, respectively, outliers may be ignored. Long-term maximum and minimum baseline impedances may alternatively be determined based on a median value of the maximum or minimum measurements, respectively, a percentage of a median value, or other function of the long-term maximum and minimum impedances. A new baseline is created each week using the most recent eight weeks, forming a sliding baseline window.

Other impedance trend parameters may be alternatively or additionally be determined such as impedance variability, slopes of short-term or long-term impedance measurements versus time, etc. Once parameters representing the short-term and long-term impedance trends have been obtained, subsequent periodic impedance measurements may be compared to these trend parameters to determine if a lead-related condition is present. Thus, method 400 of FIG. 9A may continue to method 450 of FIG. 10.

Figure 10:
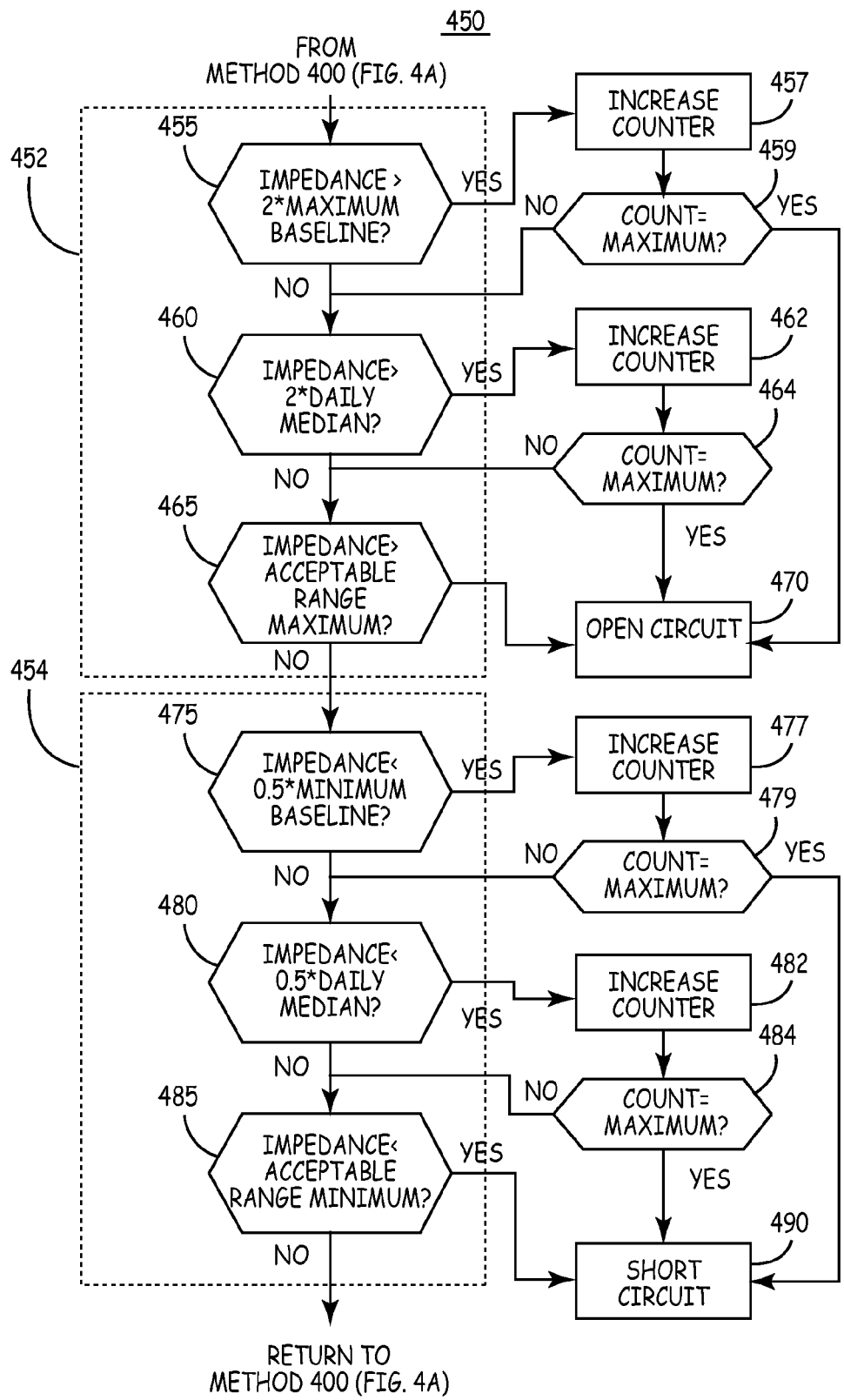
FIG. 10 is a flow chart of a method of monitoring impedance to detect an open or short circuit according to an embodiment of the present invention.

FIG. 10 is a flow chart of a method of monitoring impedance to detect an open or short circuit according to an embodiment of the present invention. As illustrated in FIG. 10, the decision Blocks 455, 460 and 465 are included in an analysis 452 for determining if an open circuit is indicated. At Block 455, a long-term periodic impedance measurement is compared to a long-term maximum baseline measurement. According to an embodiment of the present invention, each subsequent daily impedance measurement is compared to the median daily impedance Block 440 and each subsequent weekly maximum impedance measurement is compared to the weekly maximum baseline impedance, Block 441, determined according to the method 400 described above, so that subsequent daily measurements are compared to the daily median and subsequent weekly measurements are compared to the weekly baselines. If the current weekly maximum impedance measurement is significantly greater than the weekly maximum baseline, Block 441, for example 2 times greater, a counter that has been previously initialized to 0 (not shown) is increased by one count at Block 457. Once the counter reaches a predetermined maximum as determined at decision Block 459, an open circuit is detected at Block 470. In one embodiment, an open circuit is detected if three weekly maximum impedance measurements exceed twice the weekly maximum baseline.

If the periodic impedance measurement does not significantly exceed the long-term maximum baseline, or if the counter of Block 457 has not reached the predetermined maximum, the current short-term impedance measurement is compared to the short-term median impedance at decision Block 460. For example, according to the embodiment illustrated in FIG. 9B, a daily impedance measurement is compared to the median of the 14 most recent daily measurements. If the current short-term measurement is significantly greater than the short-term median, for example more than twice the short-term median, a counter that has been previously initialized to 0 (not shown) is increased by one at Block 462. Once the counter reaches a maximum, as determined at decision Block 464, an open circuit is detected at Block 470. In one embodiment, an open circuit is detected if three periodic short-term impedance measurements exceed twice the short-term median impedance.

If the periodic measurement does not significantly exceed the short-term median impedance, or if the counter of Block 464 has not reached the maximum, the periodic short-term measurement is compared to a maximum acceptable impedance, at Block 475, which may be a fixed, predetermined value or a programmable value selected based on the type of lead used. In one embodiment, an open circuit is detected at Block 470 if the daily pacing impedance measurement exceeds 2000 ohms.

Thus an open circuit may be detected based on a single impedance measurement being outside of a predetermined range associated with either a median daily impedance or a single daily impedance threshold, or, in accordance with the present invention, based on a short-term or long-term impedance trend. Diagnostic criteria set for detecting a lead-related condition based on comparisons between a periodic impedance measurement and short-term and long-term impedance parameters may be tailored to a particular lead type. For example, the difference between a periodic lead measurement and an impedance parameter trend and the number of periodic measurements deviating significantly from an impedance parameter trend may be uniquely defined depending on the type of lead being monitored. Upon detection of an open circuit, the method 350 of FIG. 8 will store the lead-related condition along with the supporting data that led to the detection (Block 385) and may provide a recommended corrective action or generate a patient notification signal.

If an open circuit is not detected during the open circuit analysis, Block 452, the method 450 proceeds to Block 475 to begin an analysis 454 for detecting a short circuit, which includes the decision Blocks 475, 480 and 485. At Block 475, a long-term periodic impedance measurement is compared to a long-term minimum baseline measurement. According to an embodiment of the present invention, a subsequent weekly minimum impedance measurement is compared to the weekly minimum baseline impedance determined according to the method 400 described above. If the weekly minimum impedance measurement is significantly less than the weekly minimum baseline impedance, Block 442, for example less than half the weekly minimum baseline impedance, a counter, that has been previously initialized to 0 (not shown) is increased by one count at Block 477. Once the counter reaches a predetermined maximum as determined at decision Block 479, a short circuit is detected at Block 490. In one embodiment, a short circuit is detected if three daily impedance measurements are less than half the weekly minimum baseline.

If the periodic impedance measurement is not significantly less than the long-term minimum baseline, or the counter of Block 477 has not reached the maximum, the current short-term impedance measurement is compared to the short-term median impedance at decision Block 480. For example, according to the embodiment of FIG. 9B, a daily impedance measurement is compared to the median of the 14 most recent daily measurements. If the current short-term measurement is significantly less than the short-term median, for example less than half the short-term median, a counter that has been previously initialized to 0 (not shown) is increased by one at Block 482. Once the counter reaches a maximum, as determined at decision Block 484, a short circuit is detected at Block 490. In one embodiment, a short circuit is detected if three daily impedance measurements are less than half the short-term median impedance.

If the periodic measurement is not significantly less than the short-term median impedance, or if the counter of Block 48 has not reached the maximum, the periodic measurement is compared to a minimum acceptable impedance, which may be a fixed, predetermined value or a programmable value, at Block 485. In one embodiment, if the daily pacing impedance measurement is less than 200 ohms, an open circuit is detected at Block 470. Upon detection of a short circuit, method 350 of FIG. 8 will store the diagnosis and supporting data (Block 385) in memory 226 an optionally provide a recommended corrective action or generate a patient notification signal.

If an open or short circuit is not detected by method 450 of FIG. 10, the method 450 returns to Block 400 of FIG. 9A to collect the next periodic impedance measurement, update the trend parameters accordingly, and continue to test for a lead-related condition in a looping fashion. Tests for a lead-related condition may further include a more rigorous analysis of long-term trends to detect a gradually occurring condition.

Figure 11A:
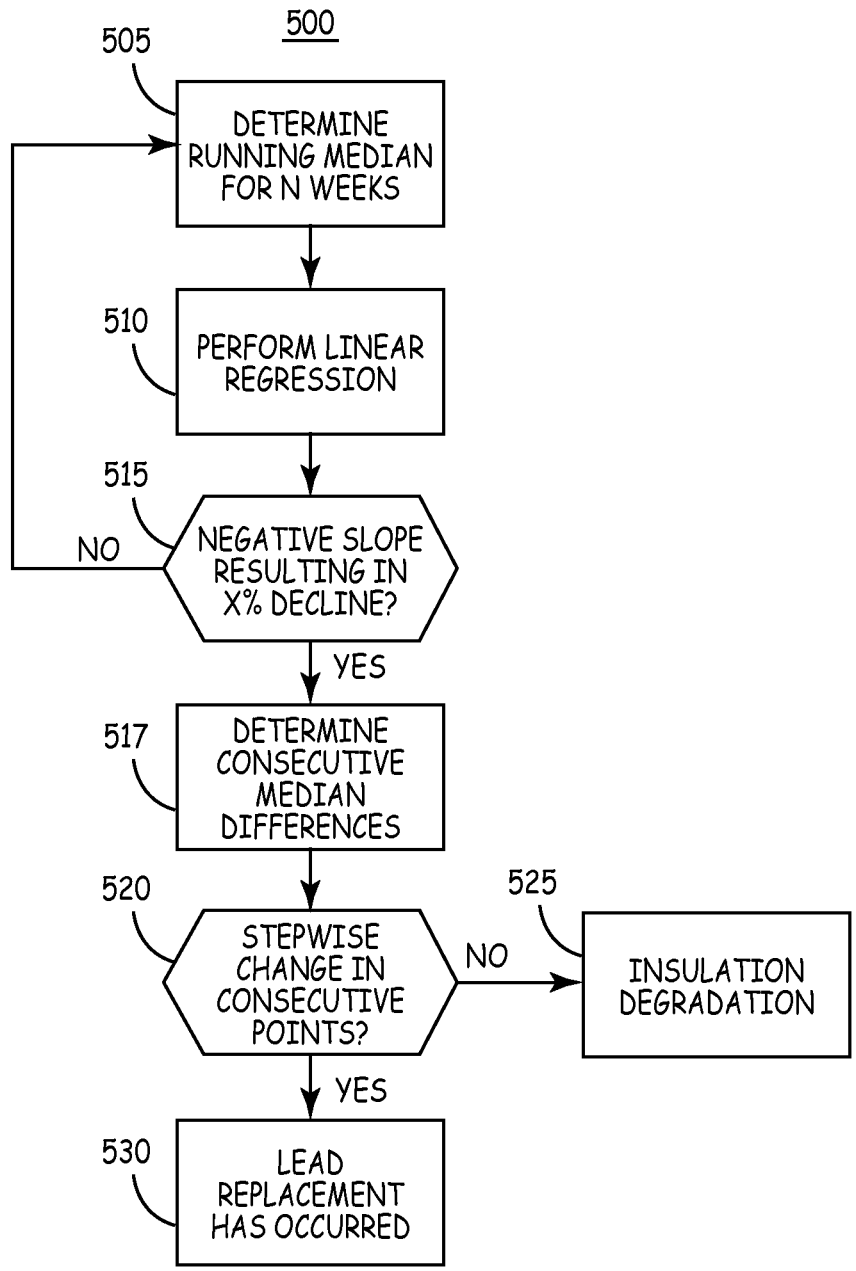
FIG. 11A is a flow chart of a method of monitoring impedance to detect insulation degradation according to an embodiment of the present invention.

FIG. 11A is a flow chart of a method of monitoring impedance to detect insulation degradation according to an embodiment of the present invention. According to the present invention, a gradual degradation of the outer insulation of a lead body may be detected by monitoring impedance trends over a relatively long-term. Method 500 begins at Block 505 by determining the running median of a given number of consecutive long-term minimum impedance measurements. In one embodiment, the median is determined from 5 weekly minimum impedance measurements. The running long-term median is then determined for a given number of terms. For example, a five-week median may be determined for 12 weeks. Next, parametric linear regression is performed on the 12 five-week median values at Block 510. The slope of the linear regression, which may be a least squares fit, is then compared to a minimum acceptable slope at decision Block 515. If a negative slope is found that represents a decrease in the impedance over the 12-week period of greater than a predetermined percentage, X, for example 30%, then a lead degradation problem is suspected. If the comparison made at decision Block 515 is not affirmed, the method 500 returns to Block 505 to continue determining a running median of the weekly minimum impedance and performing the linear regression analysis at Block 510.

If the comparison at Block 515 is affirmed, then a decline in impedance due to a lead replacement must be excluded before concluding that lead degradation condition exists. A single "step-wise" decrease in lead impedance can occur when a lead has been replaced. Therefore, to verify that the overall decrease is not due to a step-wise decrease associated with a lead replacement, the difference between each of the consecutive five-week median values used in the parametric analysis is determined at Block 517. If two consecutive medians differ by greater than a predetermined amount, for example greater than 35%, as determined at decision Block 520, then a lead replacement has occurred as concluded at Block 530. If consecutive median differences do not indicate a step-wise change, then the gradual decrease in the running median impedance is concluded to be due to insulation degradation at Block 525. This diagnosis and the supporting data are stored in memory 226 at Block 385 of method 350 (FIG. 8) for later uplinking to an external device for physician review, and a recommended action and/or a patient notification signal may be generated as described previously.

Figure 11B:
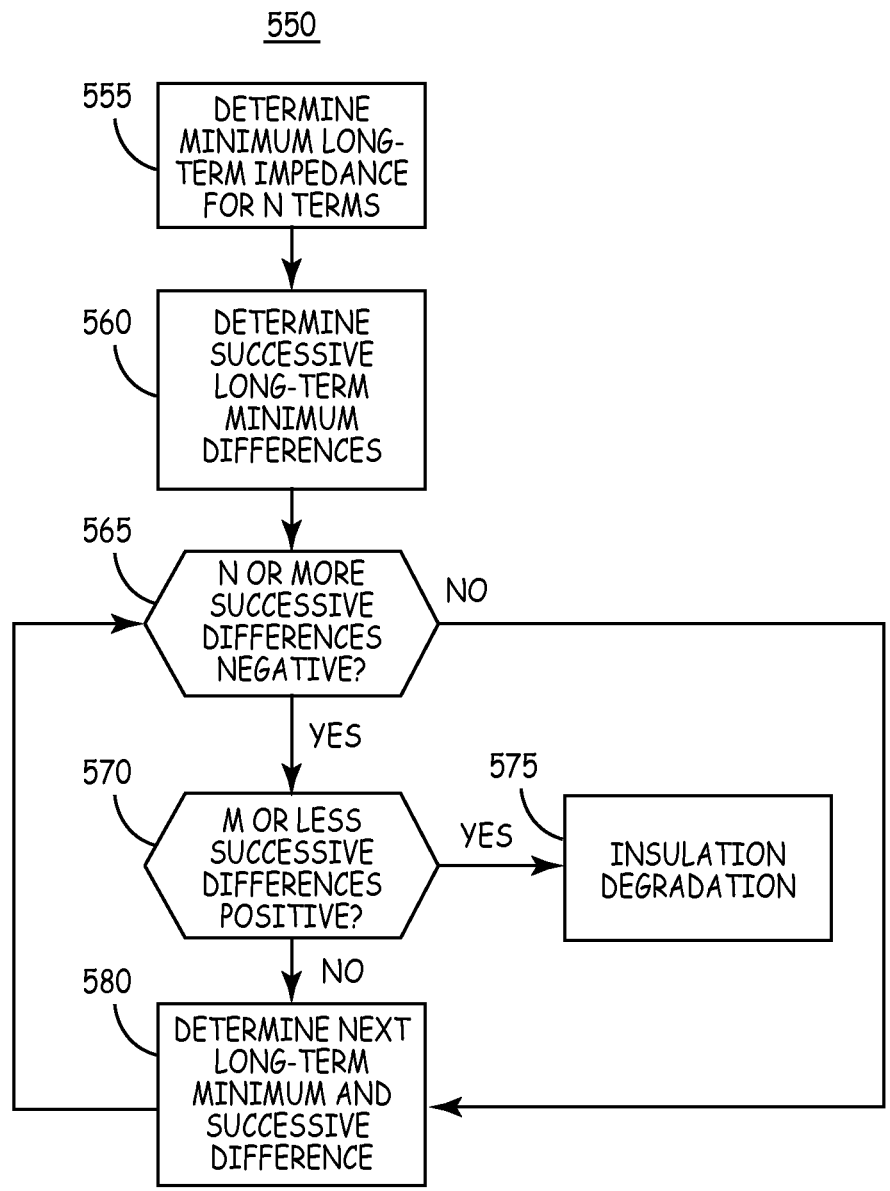
FIG. 11B is flow chart of a method for detecting lead insulation degradation using non-parametric methods according to an embodiment of the present invention.

FIG. 11B is flow chart of a method for detecting lead insulation degradation using non-parameteric methods according to an embodiment of the present invention. In method 550, the long-term minimum impedance measurement is determined for a desired number of terms at Block 555. In a preferred embodiment, a weekly minimum impedance is determined for 12 weeks. At Block 560, the successive differences between the long-term minimum impedances are determined. At decision Blocks 565 and 570, a non-parameteric analysis is performed to determine if the successive differences indicate a gradually decreasing trend of the long-term minimum impedance. In one embodiment, a given number, N, successive differences must be negative with no more than a given number, M, successive differences being positive wherein N should be greater than M. In one embodiment, if successive differences between 12 weekly minimum impedance measurements have been determined, at least five successive differences must be negative, as determined at decision Block 565, and no more than two successive differences may be positive, as determined at Block 570, in order to diagnose a lead insulation degradation condition at Block 575. If the diagnostic requirements of the non-parameteric analysis are not met at decision Block 565 and 570, the next long-term minimum impedance and associated successive difference is determined at Block 580. Method 550 then returns to Block 565 to continue monitoring the successive differences to determine if the diagnostic requirements are met.

The method 450 of FIG. 10 for detecting an open or short circuit and methods 500 or 550 of FIGS. 11A and 11B for detecting insulation degradation represent general methods that may generally be applied to many lead types. Supplementary analyses of impedance trends may be performed for detecting lead-related conditions that are characteristic of a particular lead type.

One lead related condition that can occur with certain types of leads is degradation of a middle insulation layer due to metal ion oxidation. This type of degradation is observed in leads having coaxially arranged conductors separated by polyurethane insulation. This phenomenon is not observed in other types of leads, such as leads having conductors arranged in a multi-lumen, silicone rubber lead body. Therefore, supplementary analysis of impedance trend data may include an analysis for detecting and diagnosing metal ion oxidation induced degradation. In a preferred embodiment, the type of lead in which lead impedance measurements are being made is preferably known so that appropriate supplementary analyses may be made. The lead type may be entered manually as a lead model number upon implantation by the physician. If the lead type is not known, supplementary analyses preferably include tests that will exclude types of leads that would not be subject to the particular type of lead-related condition being investigated.

Figure 12:
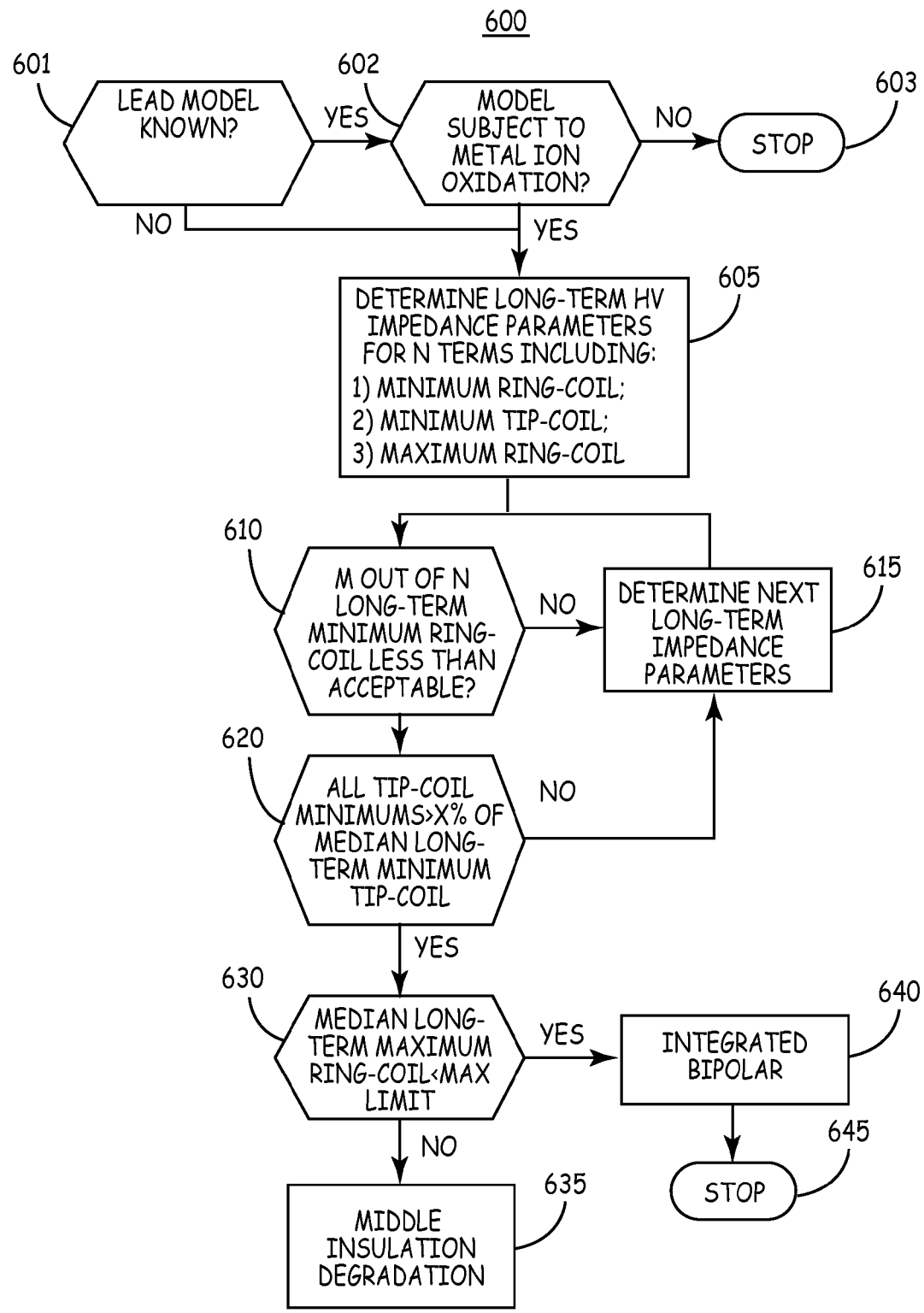
FIG. 12 is a flow chart of a method for monitoring trends in lead impedance parameters to detect middle insulation degradation due to metal ion oxidation according to an embodiment of the present invention.

FIG. 12 is a flow chart of a method for monitoring trends in lead impedance parameters to detect middle insulation degradation due to metal ion oxidation according to an embodiment of the present invention. Because this type of lead-related condition is specific to certain lead designs, method 600 begins at decision Block 601 to determine if the lead model in which lead impedance measurements are being made is known. If the lead model is not known, the method 600 may continue with the analyses but preferably includes steps for excluding leads not subject to metal ion oxidation (MIO) as will be described below.

If the lead model is known, method 600 determines if the model is subject to MIO at decision Block 602. The known lead model number may be compared to a list of lead model numbers known to be subject to MIO. If the lead model is not subject to MIO, method 600 is terminated at Block 603. If the lead is subject to MIO, method 600 continues to Block 605 to begin analyzing impedance trends.

In order to specifically diagnose middle insulation degradation, the trend of multiple lead impedance parameters is monitored. At Block 605 long-term impedance parameters are determined for multiple impedance measurement pathways. Middle insulation degradation due to MIO is typically observed in true bipolar defibrillation leads having polyurethane insulation between a coil electrode and a ring electrode. When this insulation layer begins to degrade, the impedance pathway along any pathway that includes the ring electrode and/or the coil electrode is affected. At Block 605, multiple long-term high-voltage (HV) impedance parameters are determined for a predetermined number of terms, N. The parameters preferably include a long-term minimum across ring and coil electrodes, a long-term minimum across the coil and can electrodes, and a long-term maximum across the ring and coil electrodes. In a preferred embodiment, the long term is a term of one week, and weekly parameters are collected for seven weeks.

At decision Blocks 610, 620 and 630, three criteria for diagnosing middle insulation degradation due to MIO are tested. The first criterion, tested at decision Block 610, is that a given number M, of the N long-term minimum ring-to-coil impedances must be less than an acceptable level, which would indicate a short between the ring and coil electrodes due to degradation of the intervening insulation. In a preferred embodiment, any four out of seven consecutive weekly minimum ring-to coil impedances must be lower than 14 ohms. If this criterion is not met, method 600 continues to Block 615 to determine the next long-term impedance parameters which will be stored in a rolling memory buffer designated for storing the most recent N parameters. After storing the new weekly parameters, the tests for MIO are repeated.

If the first criterion at decision Block 610 is satisfied, the second criterion is tested at decision Block 620. The second criterion is that each long-term minimum coil-can impedance is greater than a predetermined percentage of the median minimum coil-can impedance determined from the N terms. In a preferred embodiment, each weekly minimum coil-can impedance must be greater than 50% of the median of seven consecutive weekly minimum coil-can impedances. If any of the weekly minimum coil-can impedances is less than half of the median minimum coil-can impedance, then a short of the outer coil insulation may be present. An outer insulation problem will be detected and diagnosed by the methods described previously for detecting a short or general insulation degradation. When the second criterion is not met, the method 610 proceeds to Block 615 to determine the next long-term impedance parameters and will continue to monitor the impedance parameters according to the MIO diagnostic criteria.

If the second criterion is met, thereby ruling out that the decrease in the ring-coil minimum impedances found at decision Block 610 is not due to an outer insulation breach of the coil electrode, middle insulation degradation to MIO is likely to be present. The final criterion, tested at decision Block 630, is included in the case that the lead model number is not known. If the lead model number is not known, the lead in which impedances are being measured may be an integrated bipolar lead rather than a true bipolar lead. Middle insulation degradation due to MIO has not been observed in an integrated bipolar lead. Therefore, the third criterion is provided to establish that the lead is not an integrated bipolar lead.

The ring-coil impedances measured in an integrated bipolar lead will be considerably lower than the ring-coil impedances measured in a true bipolar lead. Therefore one way to discriminate between an integrated and true bipolar lead is to monitor the maximum long-term ring-coil impedance. If this maximum remains in a lower range, typical of an integrated bipolar lead, then the lead is known to be an integrated bipolar lead, generally not subject to MIO, rather than a true bipolar lead. Conversely, if the maximum long-term ring-coil impedance remains in a higher range, associated with a true bipolar lead, then the lead is known to be a true bipolar lead that is subject to MIO.

At decision Block 630, a median of a desired number of maximum long-term ring-coil impedances is compared to a predetermined maximum limit that is considered an upper boundary for the maximum ring-coil impedance of an integrated bipolar lead. In a preferred embodiment, the median of seven weekly maximum ring-coil impedances must be less than 5 ohms if the lead is an integrated bipolar lead. If this comparison is true, the lead is known to be an integrated bipolar lead as indicated at Block 640. No middle insulation condition is diagnosed.

If the comparison at decision Block 630 is not true, then the final criterion for diagnosing middle insulation degradation due to MIO in a true bipolar lead is satisfied as indicated at Block 635. This diagnosis and supporting data may be stored in memory 225 and a recommended corrective action, which would generally be lead replacement or addition of a ventricular pace/sense lead, may be indicated. A patient notification signal may be generated.

Thus, a lead-specific condition, such as middle insulation degradation due to MIO, may be diagnosed by monitoring multiple lead impedance measurement trends. This supplementary monitoring of impedance trends may be performed in addition to monitoring one or more individual lead impedance measurement trends for diagnosing general lead-related conditions associated with sudden or gradually occurring short or open circuits.

Figure 13:
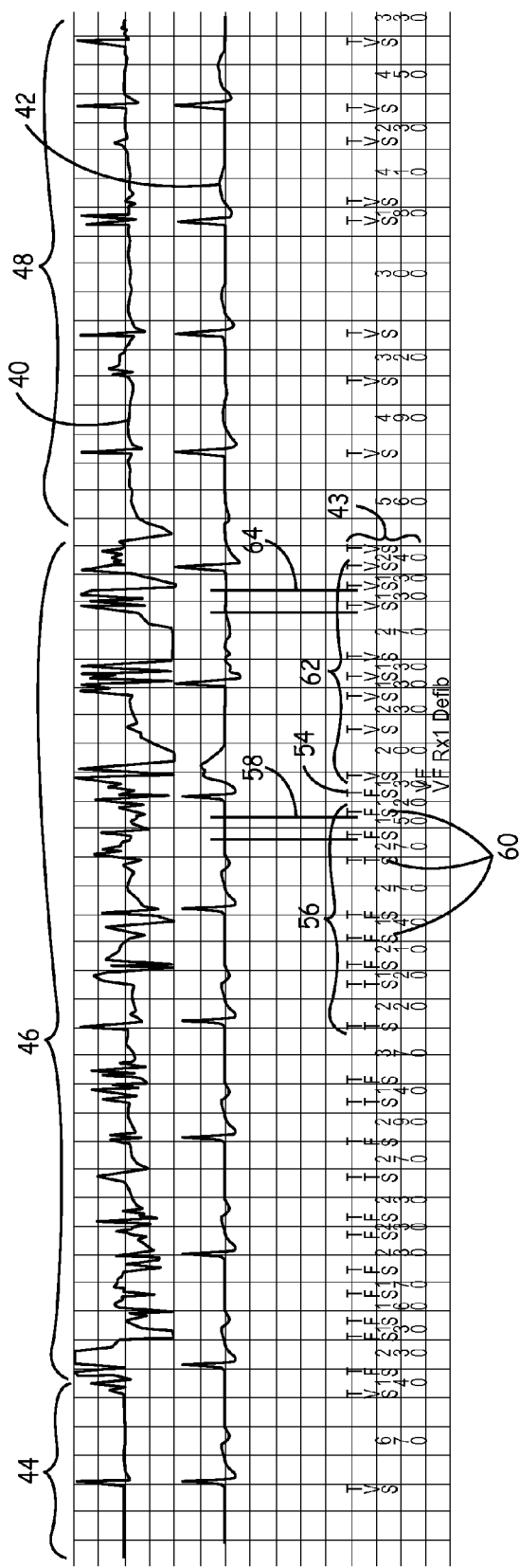
FIG. 13 is a portion of a stored electrogram showing near-field and far-field pulses where there is an indication of a false positive near-field pulse.

FIG. 13 is a portion of a stored electrogram showing near-field and far-field pulses where there is an indication of a false positive near-field pulse. As illustrated in FIG. 13, the near-field signal 40 is recorded between the tip and ring electrodes of the bipolar sensing lead, such as electrodes 24 and 26, for example. This signal is input to a sense amplifier that senses voltages that exceed a threshold. The far-field signal 42 is recorded between secondary electrodes such as the lead coil and the can or a sensing lead in another part of the heart (left auricle or right ventricle). A marker channel 43 below far-field electrogram 42 displays each sensed event from the near-field signal, such as Fibrillation Sense (FS), Fibrillation Detected (FD), Tachycardia Sensed (TS) Ventricular Sense (VS) Capacitors charged (CE), or Capacitor Discharged (CD) for example. The numbers below the letters on marker channel 43 indicate the time between sensed events. For example on the left side of FIG. 3 there are two VS events, and the number below and between them is "670", indicating that there were 670 milliseconds between the two VS events. Note that at the left of the electrogram wave 40 is a relatively normal R-wave representation 44. The period of relative normal R-wave representation 44 is followed by a series of erratic signals 46 that indicate an oversensing problem (i.e., a fractured lead conductor or insulation break on the lead).

An examination of far-field signal 42, however, shows a relatively regular far-field R-wave. During the period of relative normal R-wave representation 44, the far-field signal 42 follows the near-field signal 40 quite closely. When the near-field signal 40 becomes erratic in an erratic portion 46, the far-field signal 42 continues to show regular R-wave far-field pulses indicating that the erratic portion 46 may be due to oversensing. As the near-field signal 40 recovers at a period of relative normal R-wave representation 48, the far-field signal 42 continues to follow the near-field signal 40, suggesting that the irregular portion 46 of the near-field signal 40 was due to oversensing, and probably an intermittent failure, since the R-wave pulses of near-field signal 40 recovered at a period of relative normal R-wave representation 48.

With a pattern of this nature, it would be premature to deliver a therapy to the patient, particularly a painful defibrillation shock, in response to erratic portion 46 sensed in far-field signal 40. Typically several methods are used to avoid delivering a shock under these conditions. First, if there is a detection of an irregularity as seen in the erratic portion 46 of near-field signal 40, one can wait to see whether the problem goes away by increasing the number of intervals for detection (as is the case in the waves of FIG. 13), which would suggest that the problem may be an oversensing problem and not an arrhythmia. Also, the sensing lead electrode configuration could be changed, and pacemakers may be programmed to automatically change the sensing lead configuration (e.g. bipolar to unipolar). Finally, the patient could be given an alert (a vibration or audio alert, for example) to advise the patient to see his doctor to have the ICD and its leads checked, but an alert would not prevent the shock at the moment of oversensing.

Figure 14:
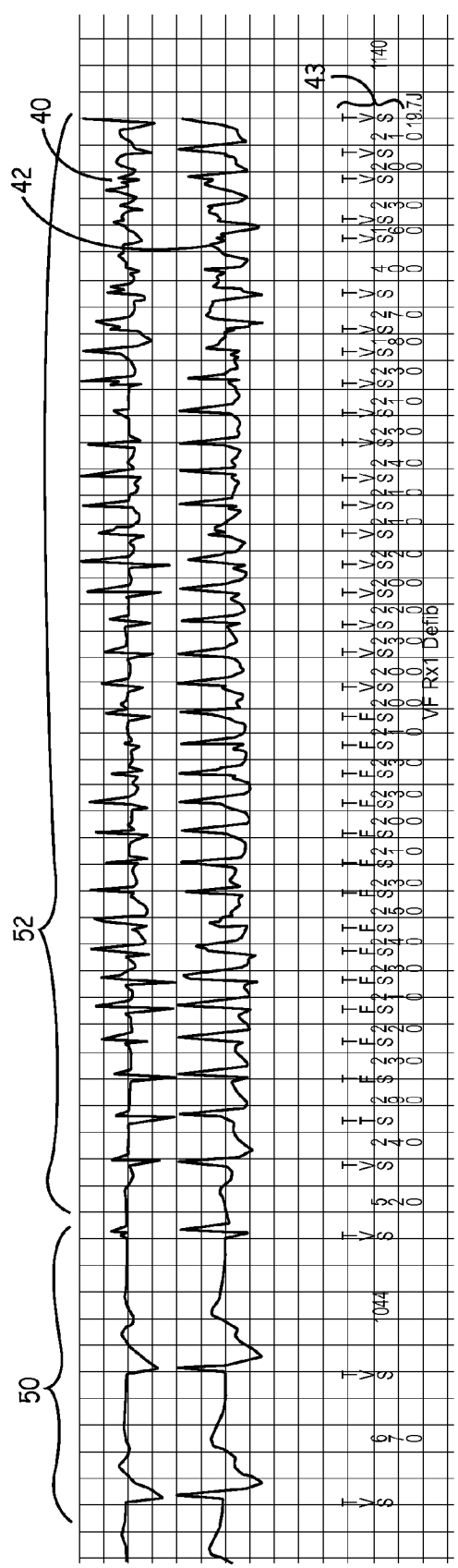
FIG. 14 is a portion of an electrogram showing near-field and far-field R-wave sensing pulses where there is an actual cardiac episode requiring therapy.

FIG. 14 is a portion of an electrogram showing near-field and far-field R-wave sensing pulses where there is an actual cardiac episode requiring therapy. The near-field signal 40 and the far-field signal 42 are shown as in FIG. 13. In this case the beginning (left side) of near-field signal 40 shows relatively normal R-waves in portion 50, although the pulses are inverted from those of FIG. 13. Likewise far-field signal 42 confirms the regularity during portion 50. At portion 52 of the near-field signal 40, however, a highly irregular waveform exists. Unlike in FIG. 3, however, the far-field wave 42 does not maintain a regular R-wave periodicity during portion 50, but rather confirms the irregularity of near-field signal 40. This would strongly suggest an arrhythmia in the patient's ventricle and call for therapy in the form of a defibrillation shock. As above, however, certain intermediate steps may be taken before actually administering the shock such as waiting a short period of time (perhaps ten or fifteen seconds) to see whether the situation resolves itself. This period of time occurs because the capacitors are charging. If in fact this waveform identifies an arrhythmia event, a therapy must be administered very quickly.

The decision to administer a therapy has been based primarily upon the near-field R-wave. The present invention uses the far-field electrogram to discriminate QRS complexes between supraventricular (e.g. sinus tachycardia, atrial fibrillation) and ventricular arrhythmias. In this way, the present invention provides an algorithm that takes into account other information to provide a better determination of an actual arrhythmia before subjecting a patient to a painful defibrillation shock.

Figure 15:
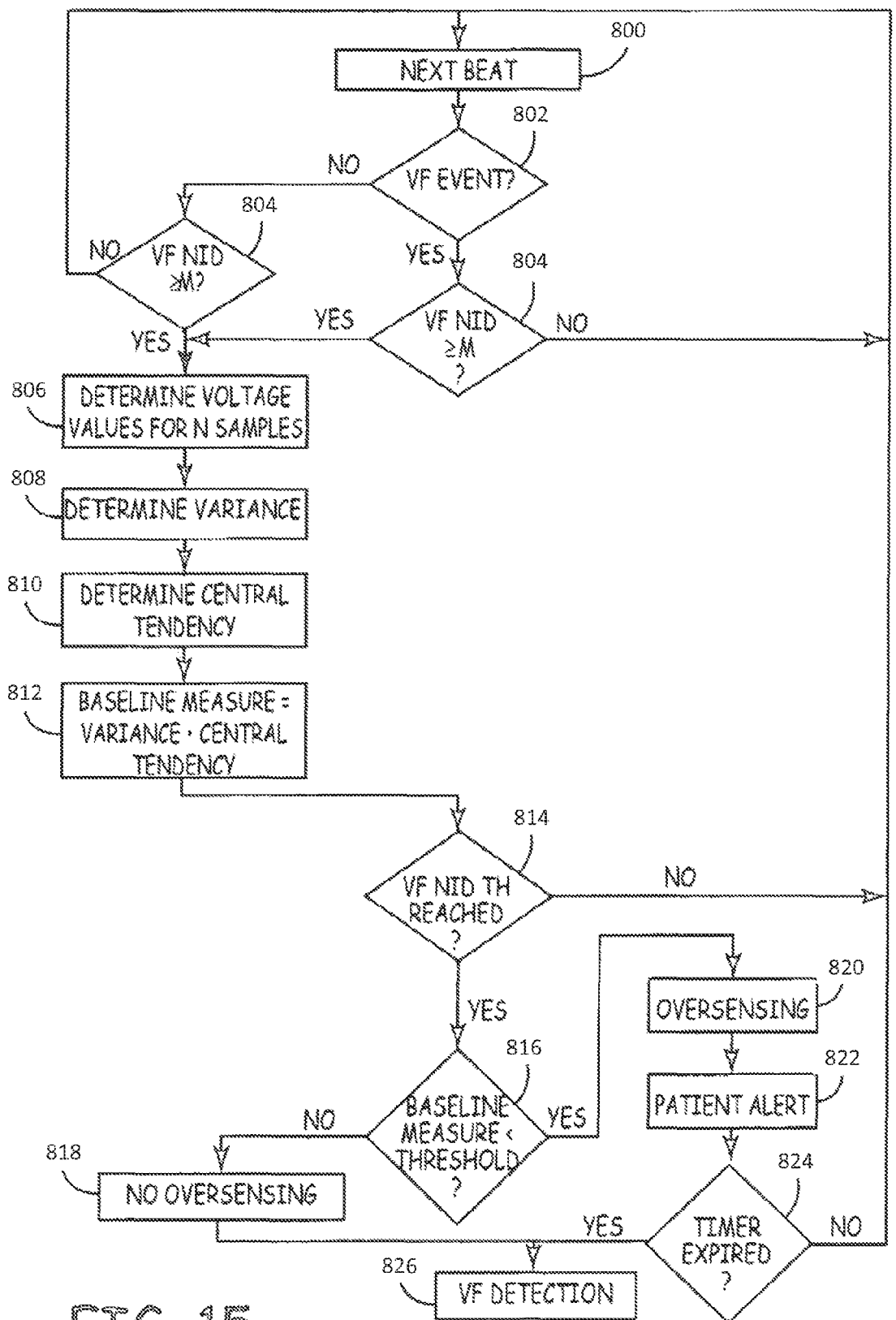
FIG. 15 is a flow chart of a method for determining the presence of oversensing in a method for of delivering a therapy in an implantable medical device, according to an embodiment of the present invention.

FIG. 15 is a flow chart of a method for determining the presence of oversensing in a method for of delivering a therapy in an implantable medical device, according to an embodiment of the present invention. Once the lead-related condition has been detected, as described above, the subsequent determination of whether oversensing is taking place (Block 342 of FIG. 3) is initiated by beginning sensing between the identified sensing electrodes for near-field and far-field sensing. In particular as illustrated in FIG. 14, each time a V-sense signal is sensed between a near-field sensor, i.e., electrodes 24 and 26 corresponding to a next beat, Block 800, a determination is made as to whether the sensed event is a VF event, with a counter corresponding to the number of sensed events and number of VF events being incremented in order to generate a number of intervals for detection of ventricular fibrillation (VF NID), Block 802. In either case, i.e., the event is not a VF event or the event is determined to be a VF event, a determination is made as to whether a predetermined number of VF events M have been detected, Block 804, by determining whether the number of intervals for detection of ventricular fibrillation is greater than the predetermined number M. If the predetermined number of VF events M has not been detected, NO in Block 804, the process waits for the next beat to occur, Block 800. Once the predetermined number of VF events M have been detected, YES in Block 804, a baseline measure associated with a far-field signal associated with the beat that is sensed between secondary electrodes is determined, Blocks 806-812, as described below. The secondary electrodes for sensing the far-field signal can include the lead coil 20 and the uninsulated portion of the housing 11, for example, or a sensing lead 6, 15 in another part of the heart alone or in combination with the uninsulated portion of the housing 11. In addition, the far-field sensing electrodes could also include one of the near-field electrodes.

According to one embodiment of the present invention, for example, the predetermined number M is set as three events so that once three VF events are detected, a baseline measure is determined, Blocks 806-812, for each subsequently sensed beat.

Figure 16B:
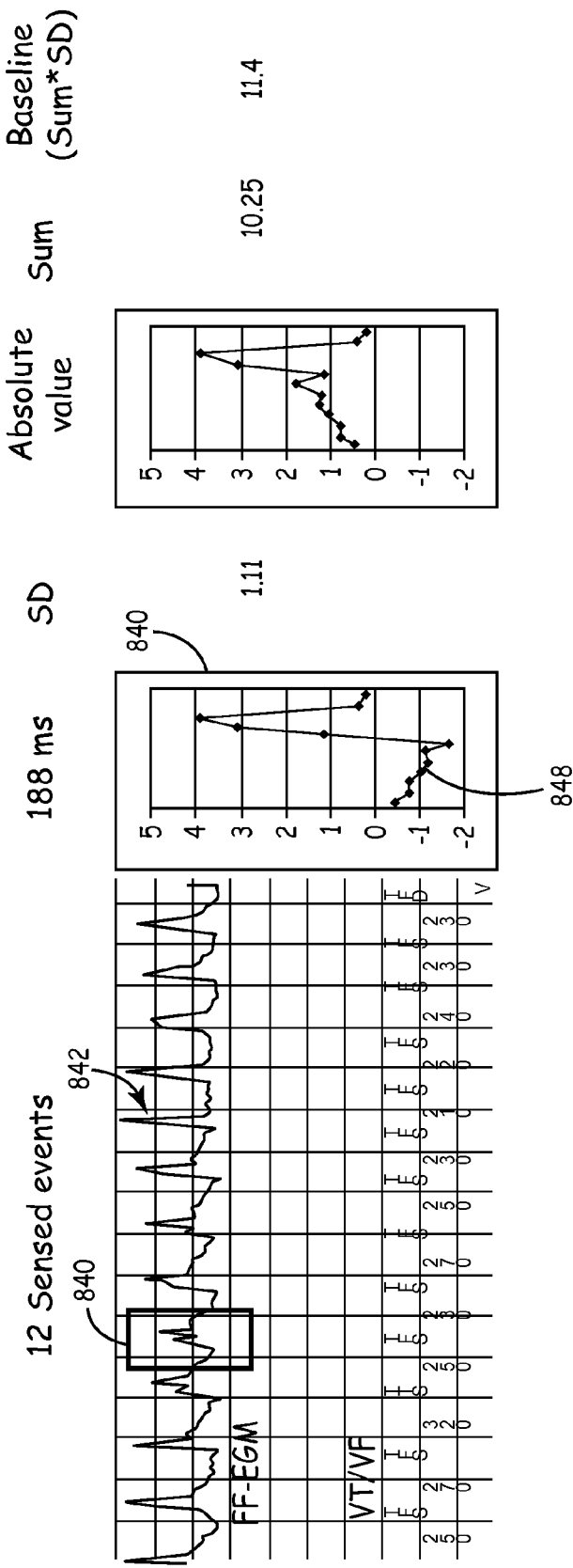

FIGS. 16A and 16B are graphical representations of a determination of a baseline measure of a far-field signal according to an embodiment of the present invention. In particular, as illustrated in FIGS. 15, 16A and 16B, in order to determine the baseline measure for the sensed beats occurring after the predetermined number of VF events M have been detected, amplitude values associated with a predetermined number of samples located within a predetermined window 840 of a far-field signal 842 that is centered around the sensed beat 844 are determined, Block 806. According to an embodiment of the present invention, window 840 is set as a 188 ms window, for example, so that amplitude values are determined for 12 samples using a 64 Hz sampling rate.

Both a variance, such as a standard deviation SD, for example, of the amplitudes of the 12 samples, Block 808, and a central tendency, such as a mean, a median, or a sum, for example, of the absolute values of the amplitudes of the twelve samples, Block 810, is determined, and so that the baseline measure is calculated using the product of the variance and the central tendency of the absolute values, Block 812.

In addition to calculating a baseline measure associated with the current sensed beat, a determination is made as to whether the VF NID is greater than a predetermined threshold, Block 814. For example, according to an embodiment of the present invention, a determination is made in Block 814 as to whether 18 out of the last 24 beats were determined to be VF events. If the VF NID threshold is not reach, NO in Block 814, the process waits for the next beat to be sensed, Block 800. Once the VF NID threshold has been met, YES in Block 814, a determination is made as to whether the baseline measure determined for any of a predetermined number of previously sensed beats, such as the last twelve beats, for example, is less than a predetermined threshold, Block 816. If none of the baseline measures associated with the predetermined number of previously sensed beats is less than the predetermined threshold, NO in Block 816, no oversensing is determined to be occurring and VF detection is confirmed, Block 818. If any one of the baseline measures associated with the predetermined number of sensed beats is less than the threshold, YES in Block 816, oversensing is determined to likely be occurring, Block 820, such as would result from a lead integrity failure, for example, and a patient alert, such as a vibration or audio alert, a wireless signal transmitted to a remote monitor, satellite, internet, for example, is activated to alert the patient, Block 822, and to advise the patient to see his doctor to have the ICD and its leads checked. Because the alert is not intended to prevent the shock at the moment of oversensing, the process is repeated for the next beat, Block 800, until a predetermined time period associated with the charging of the capacitor(s) for delivering the shock, such as 10 seconds, for example, has expired, YES in Block 824. Once the timer has expired, the VF detection process for delivering a corresponding shock therapy continues according to the normal VF detection process, Block 826, and therapy is delivered as determined necessary.

According to an embodiment of the invention, once it is determined that the patient is experiencing a VF event, i.e., the VF NID is greater than the threshold (18 of last 24 beats are determined to be VF events) and oversensing is determined, the device begins charging of one or more capacitors for delivering the therapy to the patient. According to another embodiment of the invention, once it is determined that oversensing is likely to be occurring, charging of the capacitors may be withheld until the timer of Block 824 has expired, for example.

FIGS. 16A and 16B are graphical representations of a determination of a baseline measure of a far-field signal according to an embodiment of the present invention. As illustrated in FIGS. 16A and 16B, in order to reduce the effects of oversensing, the present invention evaluates the corresponding far-field signal to determine whether a VF episode is also indicated in the far-field signal, so that if the VF NID threshold is met in Block 816 due to oversensing rather than the occurrence of a VF episode, such as when there is a loss in lead integrity resulting from lead fractures, corrupted connector interfaces, EMI issues, R-wave oversensing, myopotentials, etc., the patient is alerted of the possible oversensing issue. In particular, when VF is detected in the signal sensed by the near-field sensor but not in the signal detected by the far-field sensor 842, the standard deviation of the amplitudes of the samples in the associated window 840 and the absolute values of the amplitudes will be negligible since the far-field signal will likely approach the isoelectric baseline value of the far-field EGM signal, as illustrated in FIG. 16A. However, when VF is detected both in the signal sensed by the near-field sensor and in the signal detected by the far-field sensor 842, the standard deviation of the amplitudes of the samples in the associated window 840 and the absolute values of the amplitudes will be greater. Therefore the product of the standard deviation and the sum of the absolute values, Block 812, will be small when there is oversensing compared to when an actual arrhythmia event is occurring. In particular, according to an embodiment of the present invention, the threshold of Block 816 is set equal to one, so that if the product of the standard deviation and the sum of the absolute values is less than one for any of the predetermined number of previously sensed events, it is likely that the isoelectric baseline of the far-field signal is occurring and therefore oversensing is likely occurring.

Figure 17:
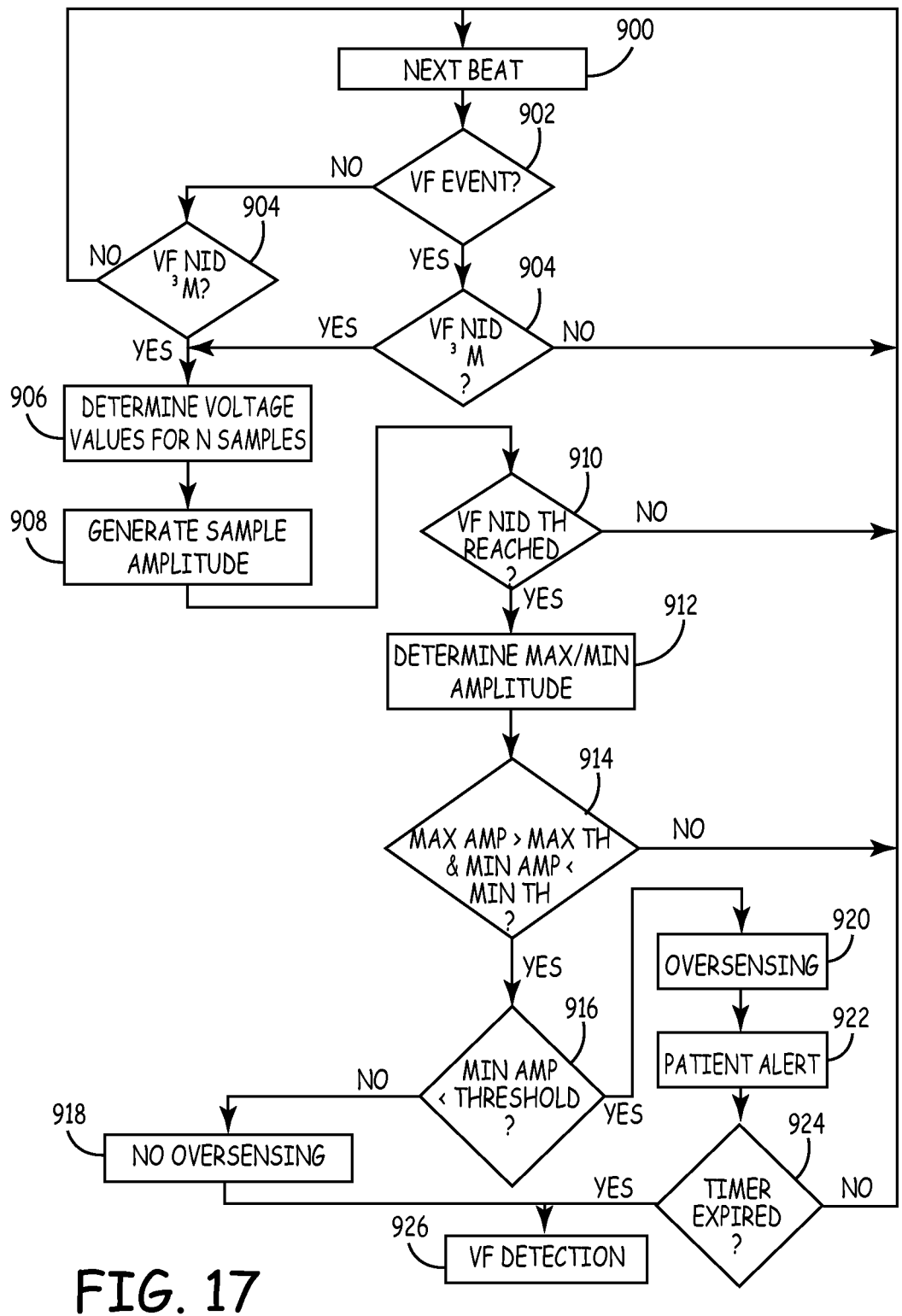
FIG. 17 is a flow chart of a method for determining the presence of oversensing in a method for delivering a therapy in a medical device, according to an embodiment of the present invention.

FIG. 17 is a flow chart of a method for determining the presence of oversensing in a method for delivering a therapy in a medical device, according to an embodiment of the present invention. As illustrated in FIG. 17, according to an embodiment of the present invention each time a V-sense signal is sensed between a near-field sensor, i.e., electrodes 24 and 26 corresponding to a next beat, Block 900, a determination is made as to whether the sensed event is a predetermined event, such as a VF event, for example, with a counter corresponding to the number of sensed events and number of VF events being incremented in order to generate a number of intervals for detection of the predetermined event, i.e., ventricular fibrillation (VF NID), Block 902. In either case, i.e., the event is not a VF event or the event is determined to be a VF event, a determination is made as to whether a predetermined number of VF events M have been detected, Block 904, by determining whether the number of intervals for detection of ventricular fibrillation is greater than the predetermined number of VF events M. According to one embodiment of the present invention, for example, the predetermined number of VF events M is set as three events.

If the predetermined number of VF events M has not been detected, NO in Block 904, the process waits for the next beat to occur, Block 900. As illustrated in FIGS. 17, 16A and 16B, once the predetermined number of VF events M have been detected, YES in Block 904, amplitude values associated with a predetermined number of samples located within a predetermined window 600 located over a portion of the far-field signal 842 and centered around the current sensed beat 844 are determined, Block 906. Window 840 is set as a 188 ms window, for example, so that amplitude values are determined in window 840 for 12 samples using a 64 Hz sampling rate to generate 12 amplitude values 848 associated with each window 840.

Once the 12 amplitude values 848 have been determined, a sample amplitude is generated for the current sensed event, Block 908, by determining a maximum amplitude and a minimum amplitude of the 12 amplitude values 848 for the far-field window 840 associated with the sensed event, and determining the difference between the maximum amplitude and the minimum amplitude. The process is repeated for the next sensed beats, generating a sample amplitude for each of the subsequently sensed events. Once the sample amplitude is generated for the sensed beat, a determination is made as to whether an episode requiring therapy, such as ventricular fibrillation for example, is detected by of determining whether the VF NID is greater than a predetermined threshold, Block 910. For example, according to an embodiment of the present invention, an episode requiring therapy is determined to be present in Block 910 when 18 out of the last 24 beats are determined to be VF events. If the VF NID threshold is not reach, NO in Block 910, the process waits for the next beat to be sensed, Block 900 and is repeated for the next sensed beat.

Once an episode requiring therapy is detected, i.e., the VF NID threshold has been met, YES in Block 910, a maximum sample amplitude and a minimum sample amplitude associated with a predetermined number of the sensed events 846, such as 8 sensed events, for example, is determined, Block 912. Although the predetermined number of sensed events 846 illustrated in FIG. 16A is shown as including eight sensed events, it is understood that the maximum sample amplitude and a minimum sample amplitude of any desired number of sensed events could be utilized and the invention is not intended to be limited to the use of eight sensed events. A determination is then made as to whether the maximum sample amplitude is greater than a predetermined maximum sample amplitude threshold, such as 2 mv for example, and the minimum sample amplitude is less than a predetermined minimum sample amplitude threshold, such as 1 mv for example, Block 914.

If the maximum sample amplitude is not greater than the predetermined maximum sample amplitude threshold or the minimum sample amplitude is not less than the predetermined minimum sample amplitude threshold, NO in Block 914, the process waits for the next beat to be sensed, Block 900, and is then repeated for the next sensed event. If the maximum sample amplitude is greater than the predetermined maximum sample amplitude threshold and the minimum sample amplitude is less than the predetermined minimum sample amplitude threshold, YES in Block 914, a determination is made as to whether the minimum sample amplitude is less than a predetermined percentage of the maximum sample amplitude, Block 916. For example, according to an embodiment of the present invention, the determination in Block 916 involves determining whether the minimum sample amplitude is less than one sixth of the maximum sample amplitude, although any desired percentage may be utilized. It is understood that although 2 mv and 1 mv are utilized as the maximum and minimum sample amplitude thresholds, respectively, any desired value may be utilized for the predetermined maximum and minimum sample amplitude thresholds.

If the minimum sample amplitude is greater than or equal to a predetermined percentage of the maximum sample amplitude, NO in Block 916, no oversensing is determined to be occurring and VF detection is confirmed, Block 918. If the minimum sample amplitude is less than a predetermined percentage of the maximum sample amplitude, YES in Block 916, oversensing is determined to likely be occurring, Block 920, such as would result from a lead integrity failure, for example, and a patient alert, such as a vibration or audio alert, a wireless signal transmitted to a remote monitor, satellite, internet, for example, is activated to alert the patient, Block 922, and to advise the patient to see his doctor to have the ICD and its leads checked. Because the alert is not intended to prevent the shock at the moment of oversensing, the process is repeated for the next beat, Block 900, until a predetermined time period associated with the charging of the capacitor(s) for delivering the shock, such as 10 seconds, for example, has expired, YES in Block 924. Once the timer has expired, the VF detection process for delivering a corresponding shock therapy continues according to the normal VF detection process, Block 926, and therapy is delivered as determined necessary.

As described above, according to an embodiment of the invention, once it is determined that the patient is experiencing a VF event, i.e., the VF NID is greater than the threshold (18 of last 24 beats are determined to be VF events) and oversensing is determined, the device begins charging of one or more capacitors for delivering the therapy to the patient. According to another embodiment of the invention, once it is determined that oversensing is likely to be occurring, charging of the capacitors may be withheld until the timer of Block 924 has expired, for example.

Figure 18:
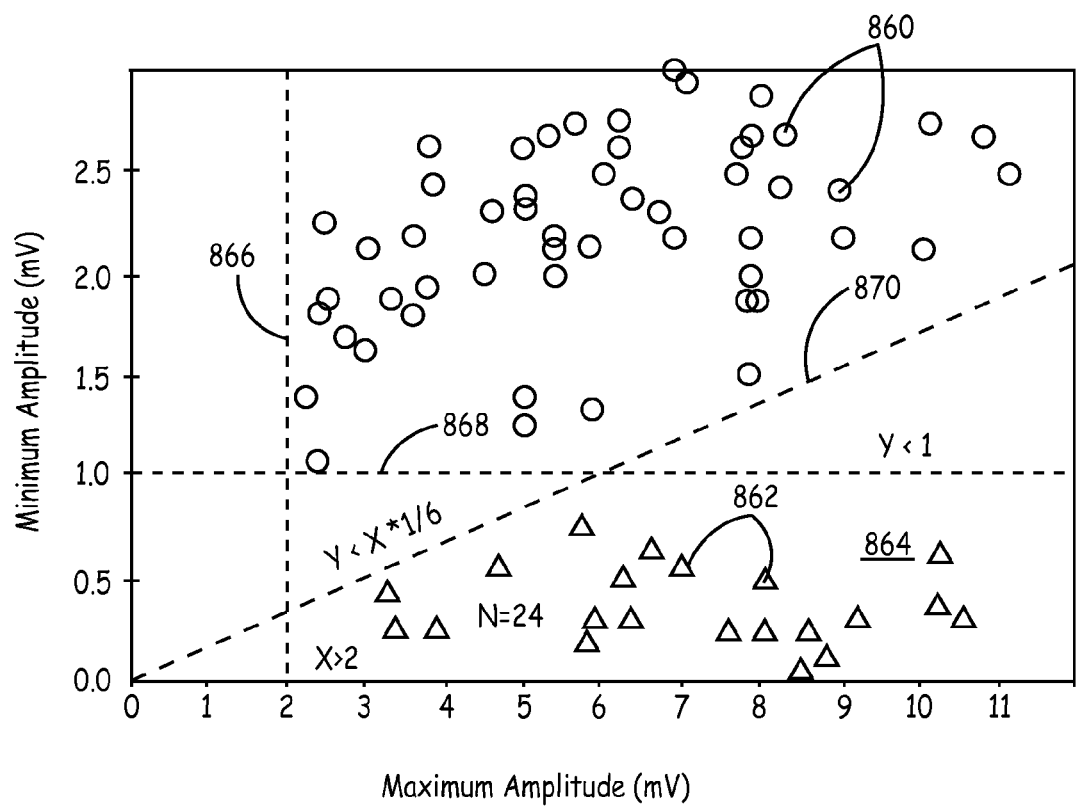
FIG. 18 is a graphical representation of maximum and minimum amplitudes of sensed events in a method of determining the presence of oversensing in a method for delivery of therapy in a medical device according to an embodiment of the present invention.

FIG. 18 is a graphical representation of maximum and minimum amplitudes of sensed events in a method of determining the presence of oversensing in a method for delivery of therapy in a medical device according to an embodiment of the present invention. In the graphical representation of FIG. 18, both actual VT/VF events 860 from a VT/VF episode and non-VT/VF events 804 that are most likely the result of oversensing caused by instances of lead failure, for example, sensed by the far-field electrode configuration are plotted on a graph of maximum amplitudes (X) versus minimum amplitudes (Y). As can be seen in FIG. 18, the non-VT/VF events 862 tend to occur within an area 864 defined by boundaries corresponding to the maximum sample amplitude being greater that 2 mv 866, the minimum sample amplitude being less that 1 mv 868, and the minimum sample amplitude being less than one sixth of the maximum sample amplitude 870, as described above.

It is understood that while the determination of the sample amplitude in Block 908 is described as being generated by determining the difference between a maximum and a minimum amplitude of the 12 amplitude values 848, the present invention may utilize other methods of determining the sample amplitudes and therefore is not intended to be limited to the determination of a maximum and a minimum amplitude as described. For example, according to an embodiment of the present invention, the sample amplitude may be determined in Block 908 using the second largest/smallest amplitude, or the third largest/smallest amplitude, etc., or may include looking at a range between values and so forth.

It is understood that other methods for detecting the presence of a lead-related condition or the presence of oversensing in Blocks 340 and 342 of FIG. 3, respectively, may be utilized, such as those set forth in commonly assigned U.S. patent application Ser. No. 10/436,626, filed May 13, 2003, entitled "Identification of Oversensing Using Sinus R-Wave Template", incorporated herein by reference in it's entirety.

Some of the techniques described above may be embodied as a computer-readable medium that includes instructions for a programmable processor such as microprocessor 224 or pacer timing/control circuitry 212 shown in FIG. 2. The programmable processor may include one or more individual processors, which may act independently or in concert. A "computer-readable medium" includes but is not limited to any type of computer memory such as floppy disks, conventional hard disks, CD-ROMS, Flash ROMS, nonvolatile ROMS, RAM and a magnetic or optical storage medium. The medium may include instructions for causing a processor to perform any of the features described above for actively determining a coupling interval according to the present invention.

The detailed description of the embodiments of the present invention provided herein yield a sensitive and specific method for diagnosing lead-related conditions based on short-term and long-term impedance trends and two measures of oversensing. It will be apparent to those skilled in the art that numerous variations of the described embodiments are possible for practicing the invention. Therefore, the embodiments described herein should be considered exemplary, rather than limiting, with regard to the following claims.

What is claimed is:

1. A method for delivering therapy in a medical device, comprising:
    determining, prior to detection of a sustained tachyarrhythmia episode, whether a lead-related condition is present;
    adjusting, in response to determining the lead-related condition is present, at least one parameter used to determine whether oversensing is present;
    detecting the sustained tachyarrhythmia episode;
    if the lead-related condition is present, determining, in response to the detection of the sustained tachyarrhythmia episode, whether oversensing is present using the at least one parameter that was adjusted in response to determining the lead-related condition is present;
    withholding delivery of a shock therapy to treat the sustained tachyarrhythmia episode in response to both determining that the lead-related condition is present and determining that oversensing is present; and
    delivering the shock therapy in response to determining that the lead-related condition is present and determining that oversensing is not present.

2. The method of claim 1, further comprising generating an alert in response to determining that the lead-related condition is present.

3. The method of claim 1, wherein determining whether the lead-related condition is present comprises:
    determining whether a first oversensing criteria is satisfied;
    determining whether a second oversensing criteria is satisfied;
    determining whether an impedance criteria has been satisfied; and
    determining the lead-related condition is present when more than one of the first oversensing criteria, the second oversensing criteria and the impedance criteria being satisfied at the same time.

4. The method of claim 3, wherein determining whether a second oversensing criteria is satisfied comprises determining whether there are a predetermined number of non-sustained tachyarrhythmia events having average cycle lengths that are less than a predetermined threshold cycle length that occur within a predetermined time period.

5. The method of claim 3, wherein determining whether an impedance criteria has been satisfied comprises:
    measuring a plurality of lead impedances;
    determining a short-term impedance trend of at least a portion of the measured lead impedances;
    determining a long-term impedance trend of at least a portion of the measured lead impedances; and
    applying a set of diagnostic criteria to the short-term and long-term impedance trends to determine whether an impedance criteria has been satisfied.

6. The method of claim 1, wherein:
    determining, prior to detection of a sustained tachyarrhythmia episode, whether a lead-related condition is present comprises determining, prior to detection of a ventricular fibrillation episode, whether a lead-related condition is present; and
    determining, in response to detection of the sustained tachyarrhythmia episode, whether oversensing is present comprises determining, in response to detection of the ventricular fibrillation episode, whether oversensing is present.

7. The method of claim 1, further comprising initiating the determining of whether oversensing is present when the lead-related condition is determined to be present.

8. The method of claim 1, wherein determining whether the oversensing is present comprises:
    obtaining a far-field signal; and
    determining whether oversensing is present using at least the obtained far-field signal.

9. The method of claim 8, wherein determining whether oversensing is present using at least the obtained far-field signal comprises:
    obtaining amplitude values associated with a predetermined number of samples within a predetermined window of the far-field signal;
    determining a variance of the obtained amplitude samples;
    determining a central tendency of the obtained samples;
    computing a baseline measure this is the product of the variance and the central tendency; and
    determining oversensing is present when the baseline measure associated with the far-field signal is less than a baseline threshold.

10. The method of claim 8, wherein determining whether oversensing is present using at least the obtained far-field signal comprises:
    obtaining a maximum sample amplitude associated with a predetermined number of far-field sensed events;
    obtaining a minimum sample amplitude associated with the predetermined number of far-field sensed events;
    determining oversensing is present when the maximum sample amplitude is greater than a predetermined maximum sample amplitude threshold, the minimum sample amplitude is less than a predetermined minimum sample amplitude threshold, and the minimum sample amplitude is less than a predetermined percentage of the maximum sample amplitude.

11. The method of claim 1 wherein adjusting the at least one parameter used to determine whether oversensing is present comprises switching the electrodes used to obtain an electrogram to include a coil electrode of a lead connected to the medical device and a housing of the medical device.

12. A system comprising:
   at least one lead; and
   an implantable medical device coupled to the at least one lead and including at least one processor configured to:
     determine, prior to detection of a sustained tachyarrhythmia episode, whether a lead-related condition is present;
     adjusting, in response to determining the lead-related condition is present, at least one parameter used to determine whether oversensing is present;
     detecting the sustained tachyarrhythmia episode;
     if the lead-related condition is present, determine, in response to the detection of the sustained tachyarrhythmia episode, whether oversensing is present using the at least one parameter that was adjusted in response to determining that the lead-related condition is present;
     withhold delivery of a shock therapy to treat the sustained tachyarrhythmia episode in response to both determining that the lead-related condition is present and determining that oversensing is present; and
     deliver the shock therapy in response to determining that the lead-related condition is present and determining that oversensing is not present.

13. The system of claim 12, wherein the processor determines whether the lead-related condition is present by:
   determining whether a first oversensing criteria is satisfied;
   determining whether a second oversensing criteria is satisfied;
   determining whether an impedance criteria has been satisfied; and
   determining the lead-related condition is present when more than one of the first oversensing criteria, the second oversensing criteria and the impedance criteria being satisfied at the same time.

14. The system of claim 13, wherein the processor is configured to determine that the second oversensing criteria is satisfied when there are a predetermined number of non-sustained tachyarrhythmia events having average cycle lengths that are less than a predetermined threshold cycle length that occur within a predetermined time period.

15. The system of claim 13, wherein the processor is configured to:
   measure a plurality of lead impedances;
   determine a short-term impedance trend of at least a portion of the measured lead impedances;
   determine a long-term impedance trend of at least a portion of the measured lead impedances; and
   apply a set of diagnostic criteria to the short-term and long-term impedance trends to determine whether an impedance criteria has been satisfied.

16. The system of claim 12, wherein the processor is configured to:
   determine, prior to detection of a ventricular fibrillation episode, whether a lead-related condition is present; and
   determine, in response to detection of the ventricular fibrillation episode, whether oversensing is present.

17. The system of claim 12, wherein the processor initiates the determining of whether oversensing is present when the lead-related condition determined to be is present.

18. The system of claim 12, wherein the processor of the implantable medical device is configured to:

obtain a far-field signal; and
   determine whether oversensing is present using at least the obtained far-field signal.

19. The system of claim 18, wherein the processor of the implantable medical device is configured to determine whether oversensing is present using at least the obtained far-field signal by:
   obtaining amplitude values associated with a predetermined number of samples within a predetermined window of the far-field signal;
   determining a variance of the obtained amplitude samples;
   determining a central tendency of the obtained samples;
   computing a baseline measure this is the product of the variance and the central tendency; and
   determining oversensing is present when the baseline measure associated with the far-field signal is less than a baseline threshold.

20. system of claim 18, wherein the processor of the implantable medical device is configured to determine whether oversensing is present using at least the obtained far-field signal by:
   obtaining a maximum sample amplitude associated with a predetermined number of far-field sensed events;
   obtaining a minimum sample amplitude associated with the predetermined number of far-field sensed events;
   determining oversensing is present when the maximum sample amplitude is greater than a predetermined maximum sample amplitude threshold, the minimum sample amplitude is less than a predetermined minimum sample amplitude threshold, and the minimum sample amplitude is less than a predetermined percentage of the maximum sample amplitude.

21. The system of claim 12, wherein the processor adjusts the at least one parameter used to determine whether oversensing is present by at least switching the electrodes used to obtain an electrogram to include a coil electrode of the at least one lead coupled to the implantable medical device and a housing of the implantable medical device.

22. A non-transitory computer-readable medium comprising instructions that, when executed by a processor, cause the processor to:
   determine, prior to detection of a sustained tachyarrhythmia episode, whether a lead-related condition is present;
   adjusting, in response to determining the lead-related condition is present, at least one parameter used to determine whether oversensing is present;
   detecting the sustained tachyarrhythmia episode;
   if the lead-related condition is present, determine, in response to the detection of the sustained tachyarrhythmia episode, whether oversensing is present using the at least one parameter that was adjusted in response to determining the lead-related condition is present;
   withhold delivery of a shock therapy to treat the sustained tachyarrhythmia episode in response to both determining that the lead-related condition is present and determining that oversensing is present; and
   deliver the shock therapy in response to determining that the lead-related condition is present and determining that oversensing is not present.

23. The non-transitory computer-readable medium of claim 22, further comprising instructions that, when executed by the processor, cause the processor to initiate the determining of whether oversensing is present when the lead-related condition is determined to be present.

* * * * *